United States Patent
Yamashita et al.

(10) Patent No.: US 10,208,287 B2
(45) Date of Patent: Feb. 19, 2019

(54) CD82-POSITIVE CARDIAC PROGENITOR CELLS

(71) Applicant: iHeart Japan Corporation, Kyoto-shi, Kyoto (JP)

(72) Inventors: Jun Yamashita, Kyoto (JP); Masafumi Takeda, Kyoto (JP)

(73) Assignee: iHeart Japan Corporation, Kyoto-shi, Kyoto (JP)

( * ) Notice: Subject to any disclaimer, the term of this patent is extended or adjusted under 35 U.S.C. 154(b) by 39 days.

(21) Appl. No.: 15/308,147

(22) PCT Filed: Apr. 16, 2015

(86) PCT No.: PCT/JP2015/002107
§ 371 (c)(1),
(2) Date: Nov. 1, 2016

(87) PCT Pub. No.: WO2015/166638
PCT Pub. Date: Nov. 5, 2015

(65) Prior Publication Data
US 2017/0067023 A1     Mar. 9, 2017

(30) Foreign Application Priority Data
May 1, 2014   (JP) .................................. 2014-094775

(51) Int. Cl.
*C12N 5/077* (2010.01)
*C12N 5/10* (2006.01)
*A61K 35/12* (2015.01)

(52) U.S. Cl.
CPC ............ *C12N 5/0657* (2013.01); *A61K 35/12* (2013.01); *C12N 5/10* (2013.01); *C12N 2506/45* (2013.01)

(58) Field of Classification Search
CPC .... C12N 5/0657; C12N 5/10; C12N 2506/45; A61K 35/12
See application file for complete search history.

(56) References Cited

U.S. PATENT DOCUMENTS

| | | | |
|---|---|---|---|
| 9,623,052 B2 | 4/2017 | Okano et al. | |
| 2012/0027807 A1* | 2/2012 | Chien | A61L 27/3804 424/400 |
| 2016/0108363 A1* | 4/2016 | Chien | G01N 33/5014 424/93.7 |

FOREIGN PATENT DOCUMENTS

| | | |
|---|---|---|
| JP | 2009254271 | 11/2009 |
| WO | 2005/063967 | 7/2005 |
| WO | 2006/093276 | 9/2006 |
| WO | 2009118928 | 10/2009 |
| WO | 2013/137491 | 9/2013 |

OTHER PUBLICATIONS de Hartogh et al. A comprehensive gene expression analysis at sequential stages of in vitro cardiac differentiation from isolated MESP1—expressing mesoderm progenitors. Scientific Reports 6, 19386; doi: 10.1038/srep19386 (2016). (Year: 2016).*
Bhartiya. Are Mesenchymal Cells Indeed Pluripotent Stem Cells or Just Stromal Cells? OCT-4 and VSELs Biology Has Led to Better Understanding. Stem Cells International vol. 2013, Article ID 547501, 6 pages (Year: 2013).*
TNFSF9. TNF superfamily member 9. NCBI. downloaded on Feb. 1, 2018 from https://www.ncbi.nlm.nih.gov/gene/8744#top. p. 1-8 (Year: 2018).*
Cyganek et al. Cardiac Progenitor Cells and their Therapeutic Application for Cardiac Repair. J Clin Exp Cardiolog S11: 008. (2013) . p. 1-12.*
Anversa et al. Circulating Progenitor Cells: Search for an Identity. Circulation 2004;110:3158-3160 (Year: 2004).*
Yamashita, Jun K., Makoto Takano, Mina Hiraoka-Kanie, Chikashi Shimazu, Yan Peishi, Kentoku Yanagi, Akiko Nakano, Emi Inoue, Fumiyo Kita, and Shin-Ichi Nishikawa. "Prospective identification of cardiac progenitors by a novel single cell-based cardiomyocyte induction." The FASEB journal 19, No. 11 (2005): 1534-1536.
English Translation of International Preliminary Report on Patentability dated Nov. 10, 2016 for corresponding PCT/JP2015/002107.
Ardehali et al., "Prospective Isolation of Human Embryonic Stem Cell-Derived Cardiovascular Progenitors that Integrate into Human Fetal Heart Disease," PNAS, Feb. 26, 2013, vol. 110, No. 9, pp. 3405-3410.
Bartosh et al., "Aggregation of Human Mesenchymal Stromal Cells (MSCs) into 3D Spheroids Enhances Their Antiinflammatory Propeties," PNAS, Aug. 3, 2010, vol. 107, No. 31, pp. 13724-13729.
Burridge et al., "Production of De Novo Cardiomyocytes: Human Pluripotent Stem Cell Differentiation and Direct Reprogramming," Cell Stem Cell 10, Jan. 6, 2012, pp. 16-28.
Kattman et al., "Stage-Specific Optimization of Activin/Nodal and BMP Signaling Promotes Cardiac Differentiation of Mouse and Human Pluripotent Stem Cell Lines," Cell Stem Cell 8, 228-240, Feb. 4, 2011.

(Continued)

*Primary Examiner* — Taeyoon Kim
(74) *Attorney, Agent, or Firm* — Occhiuti & Rohlicek LLP

(57) ABSTRACT

An object of the present invention is to provide a myocardial progenitor cell that is specifically induced to differentiate into a cardiomyocyte, and a method for preparing the myocardial progenitor cell. A method for preparing a CD82-positive cell includes, in sequence, a step (a) of obtaining stem cells, a step (b) of subjecting the stem cells to induction treatment of differentiation into cardiovascular cells, and a step (c) of separating, from the stem cells having been subjected to the induction treatment of differentiation in the step (b), a CD82-positive cell being negative for at least one cell surface marker selected from CD73, CD44, CD105, CD121a, CD18, and CD120a. This method enables preparation of a CD82-positive cell for use as a myocardial progenitor cell.

19 Claims, 13 Drawing Sheets

(56) References Cited

OTHER PUBLICATIONS

Takahashi et al., "Induction of Pluripotent Stem Cells from Mouse Embryonic and Adult Fibroblast Cultures by Defined Factors," Cell 126, 663-676, Aug. 25, 2006.
Takahashi et al., "Induction of Pluripotent Stem Cells from Adult Human Fibroblasts by Defined Factors," Cell 131, 861-872, Nov. 30, 2007.
Takeda et al., "Identification of Human iPS Cell-Derived Cardiac Progenitor Enriched Population," Regenerative Medicine, Jan. 27, 2014, vol. 13. (English Abstract Included).
Takeda et al., "Identification of a Specific Cell Surface Marker of Cardiomyocyte Committed Progenitor Population," Regenerative Medicine, Feb. 1, 2015, vol. 14. (English Abstract Included).
Uosaki et al., "Efficient and Scalable Purification of Cardiomyocytes from Human Embryonic and Induced Pluripotent Stem Cells by VCAM1 Surface Expression," PLoS One, Aug. 2011, vol. 6, Issue 8.
Yang et al., "Human Cardiovascular Progenitor Cells Develop from a KDR+ Embryonic-Stem-Cell-Derived Population," Nature, vol. 453, May 22, 2008, 524-529.

\* cited by examiner

CD82-POSITIVE CARDIAC PROGENITOR CELLS

CROSS REFERENCE TO RELATED APPLICATIONS

This application is a National Phase under 35 USC 371 of International Application No. PCT/JP2015/002107 filed on Apr. 16, 2015, which claims priority to Japanese Application No. 2014-094775 filed May 1, 2014, the contents of which are hereby incorporated by reference in their entirety.

TECHNICAL FIELD

The present invention relates to a CD82-positive cell for use as a myocardial progenitor cell, the CD82-positive cell being negative for at least one cell surface marker selected from CD73, CD44, CD105, CD121a, CD18, and CD120a; a heart disease therapeutic agent containing the CD82-positive cell; a method for preparing the CD82-positive cell; and a CD82-positive cell for use as a myocardial progenitor cell, the CD82-positive cell being obtained by the preparation method.

BACKGROUND ART

Heart disease is a leading cause of death in developed nations. For example, the Ministry of Health, Labour and Welfare reported heart disease as the second leading cause of death in Japan on the basis of statistical data on cause of death from 2011 to 2013.

Ischemic heart disease, which includes angina pectoris and myocardial infarction, is caused by insufficient blood flow to the myocardium due to coronary artery stenosis or coronary artery thromboembolism. In order to treat such ischemic heart disease, intervention treatment using a catheter to improve blood flow is performed. However, the myocardium cannot be regenerated by intervention treatment once necrosed. For this reason, there has been a clinical problem of an absence of an effective remedy for heart diseases including a morbid state of severe cardiac failure caused by a decrease in the number of viable cardiomyocytes after recovery from ischemia, and a morbid state of chronic progressive loss of cardiomyocytes occurring gradually that is not caused by ischemia and leads to cardiac failure.

Pluripotent stem cells have the potential of differentiating into all cells of an organism, and a typical example thereof is embryonic stem cells (ES cells). Because of such characteristics, human ES cells are expected to be applied to regenerative therapy including myocardial regenerative therapy. However, transplantation of differentiated ES cells may cause rejection, which is problematic.

In recent years, Yamanaka's group has reported the development of induced pluripotent stem cells having pluripotency and proliferation potency comparable to ES cells, in what is called iPS cells (induced pluripotent stem cells), which are prepared by inducing dedifferentiation of mouse somatic cells through expression of four factors (Oct3/4, Sox2, Klf4, and c-myc) (Non Patent Literature 1); and Yamanaka's group has subsequently reported that iPS cells can also be prepared from human differentiated cells (Non Patent Literature 2). Such human iPS cells can be prepared from cells derived from the patient to be treated, and hence are expected as a tool for the preparation of myocardial tissue without causing rejection. For this reason, there has been a demand for the establishment of myocardial regenerative therapy employing human iPS cells as early as possible.

In myocardial regenerative therapy employing human iPS cells, candidate cells serving as the source of supply include cardiomyocytes prepared by inducing human iPS cells to differentiate, and myocardial progenitor cells in the pre-differentiation stage.

When myocardial regenerative therapy is performed with cardiomyocytes prepared by inducing human iPS cells to differentiate, cardiomyocytes do not substantially proliferate and also exhibit a low take rate in the recipient's heart. For this reason, a cardiomyocyte sheet may be produced such that a sufficiently large number of cardiomyocytes for transplantation are prepared by inducing human iPS cells to differentiate, so that the sheet exhibits an increased take rate in the heart; and this cardiomyocyte sheet may be administered.

On the other hand, when myocardial regenerative therapy is performed with myocardial progenitor cells, the key is to isolate progenitor cells that specifically differentiate into the myocardium. As myocardial progenitor cells, for example, Gordon Keller et al. have reported KDR-positive PDGFRα-positive cells (Non Patent Literatures 3 and 4). However, KDR and PDGFRα, which are expressed also in early mesoderm, cannot be regarded as cell surface markers that enable identification of cell groups having the potential of specific differentiation into the myocardium. Recently, Irving L. Weissman et al. have reported that CD13 and ROR2 are cell surface markers for myocardial and vascular progenitor cells (cardiovascular progenitor cells) (Non Patent Literature 5). It is true CD13-positive ROR2-positive cells include cells that can differentiate into the myocardium; however, these cells also include cells that can differentiate into, other than the myocardium, the vascular endothelium or blood vessel walls. In addition, since expressions of CD13 and ROR2 are observed also in the primitive streak stage of early mesoderm, CD13 and ROR2 cannot be regarded as cell surface markers that enable identification of cell groups having the potential of specific differentiation into the myocardium. Furthermore, Nkx2.5, islet1, Tbx5, Tbx20, GATA4, MEF2C, and the like have been reported as markers for myocardial progenitor cells (Non Patent Literature 6). However, these markers are not cell surface markers, but transcription factors. For this reason, isolation of myocardial progenitor cells expressing such a transcription factor requires, for example, genetic modification. Thus, myocardial progenitor cells that are not modified cannot be isolated. There has been a report on a method of harvesting myocardial tissue, and directly selecting and isolating, from the tissue, pluripotent stem cells having a high potential of differentiation into cardiomyocytes (Patent Literature 1). However, since myocardial tissue is used as the source of supply, a sufficiently large number of cells for therapy may not be necessarily obtained, which raises a question of clinical application of the method. In addition, this method requires donors of myocardial tissue and hence is not very versatile. Therefore, there has been a demand for identification of a cell surface marker for myocardial progenitor cells having the potential of specific differentiation into the myocardium.

CITATION LIST

Patent Literature

PTL 1: International Publication No. 2006/093276 pamphlet

Non Patent Literature

NPL 1: Takahashi, K. et al., Cell 126: 663-676 (2006)
NPL 2: Takahashi, K. et al., Cell 131: 861-872 (2007)
NPL 3: Abbott, G. W. et al., Nature 453: 524-528 (2008)
NPL 4: Kattman, S. J. et al., Cell Stem Cell 8: 228-240 (2011)
NPL 5: Ardehali, R. et al., Proc Natl Acad Sci USA. 110: 3405-3410 (2013)
NPL 6: Burridge, P. W. et al., Cell Stem Cell 10: 16-28 (2012)

SUMMARY OF INVENTION

Technical Problem

An object of the present invention is to provide a myocardial progenitor cell that is specifically induced to differentiate into a cardiomyocyte, and a method for preparing the myocardial progenitor cell.

Solution to Problem

The inventors of the present invention continuously perform thorough studies on how to achieve the object. Through the studies, the inventors have found that, from day 4 to day 5 after induction treatment of differentiation from human iPS cells into cardiomyocytes, myocardial progenitor cells that specifically differentiate into cardiomyocytes begin to appear. The inventors also have found that such myocardial progenitor cells are CD82-positive cells. The inventors subjected such CD82-positive cells to in vitro and in vivo analyses and have demonstrated that the cells are always efficiently induced to differentiate into cardiomyocytes even under various culture conditions or in transplantation to various tissues and organs. These findings serve as bases to accomplish the present invention.

Specifically, the present invention relates to (1) a CD82-positive cell for use as a myocardial progenitor cell, the CD82-positive cell being negative for at least one cell surface marker selected from [Cell surface marker group A] below,
[Cell surface marker group A]
CD73, CD44, CD105, CD121a, CD18, and CD120a.

The present invention also relates to (2) the CD82-positive cell according to (1) above, being an isolated cell; and relates to (3) the CD82-positive cell according to (1) or (2) above, being negative for at least one cell surface marker selected from [Cell surface marker group B] below and/or being positive for at least one cell surface marker selected from [Cell surface marker group C] below,
[Cell surface marker group B]
CD7, CD37, CD43, CD144, STRO-1, CD177, and CD163,
[Cell surface marker group C]
CD137L, CD140b, CD180, CD252, CD344, CD118, and CD99R.

The present invention also relates to (4) the CD82-positive cell according to any one of (1) to (3) above, being negative for at least one cell surface marker selected from [Cell surface marker group D] below and/or being positive for at least one cell surface marker selected from [Cell surface marker group E] below,
[Cell surface marker group D]
CD49a, CD117, CD31, CD106, CD45, CD14, HLA-DR, CD38, CD121b, CD122, CD124, CD126, CD127, CD11a, CD104, CD62e, CD621, CD62p, CD120b, CD34, and CD4,
[Cell surface marker group E]
CD166, CD304, and CD90.

The present invention also relates to (5) the CD82-positive cell according to any one of (1) to (4) above, being positive for at least one cell surface marker selected from [Cell surface marker group F] below,
[Cell surface marker group F]
ROR2, CD13, PDGFRα, and KDR.

The present invention also relates to (6) the CD82-positive cell according to any one of (1) to (5) above, being cryopreserved.

The present invention also relates to (7) a heart disease therapeutic agent containing the CD82-positive cell according to any one of (1) to (6) above.

The present invention also relates to (8) a method for preparing a CD82-positive cell, the method including steps (a) to (c) below,
(a) a step of obtaining stem cells;
(b) a step of subjecting the stem cells to induction treatment of differentiation into cardiovascular cells; and
(c) a step of separating, from the stem cells having been subjected to the induction treatment of differentiation in the step (b), a CD82-positive cell being negative for at least one cell surface marker selected from [Cell surface marker group A] below;
[Cell surface marker group A]
CD73, CD44, CD105, CD121a, CD18, and CD120a.

The present invention also relates to (9) the preparation method according to (8) above, wherein the stem cells are human pluripotent stem cells; relates to (10) the preparation method according to (9) above, wherein the human pluripotent stem cells are human induced pluripotent stem cells; relates to (11) the preparation method according to any one of (8) to (10) above, wherein the induction treatment of differentiation into cardiovascular cells is induction treatment of differentiation into myocardial progenitor cells; and relates to (12) the preparation method according to any one of (8) to (11) above, wherein the CD82-positive cell is negative for at least one cell surface marker selected from [Cell surface marker group B] below and/or is positive for at least one cell surface marker selected from [Cell surface marker group C] below,
[Cell surface marker group B]
CD7, CD37, CD43, CD144, STRO-1, CD177, and CD163,
[Cell surface marker group C]
CD137L, CD140b, CD180, CD252, CD344, CD118, and CD99R.

The present invention also relates to (13) the preparation method according to any one of (8) to (12) above, wherein the CD82-positive cell is negative for at least one cell surface marker selected from [Cell surface marker group D] below and/or is positive for at least one cell surface marker selected from [Cell surface marker group E] below,
[Cell surface marker group D]
CD49a, CD117, CD31, CD106, CD45, CD14, HLA-DR, CD38, CD121b, CD122, CD124, CD126, CD127, CD11a, CD104, CD62e, CD621, CD62p, CD120b, CD34, and CD4,
[Cell surface marker group E]
CD166, CD304, and CD90.

The present invention also relates to (14) the preparation method according to any one of (8) to (13) above, wherein the CD82-positive cell is positive for at least one cell surface marker selected from [Cell surface marker group F] below,
[Cell surface marker group F]
ROR2, CD13, PDGFRα, and KDR.

The present invention also relates to (15) the preparation method according to any one of (8) to (14) above, wherein, in the step (c), the CD82-positive cell is separated during day 4 to day 8 after the induction treatment of differentiation performed in the step (b).

The present invention also relates to (16) a CD82-positive cell for use as a myocardial progenitor cell, the CD82-positive cell being obtained by the preparation method according to any one of (8) to (15) above.

Other embodiments according to the present invention include myocardial progenitor cells including the above-described CD82-positive cells; myocardial progenitor cell-containing compositions containing the above-described CD82-positive cells; a method for treating heart disease by administering the above-described heart disease therapeutic agent into a patient with heart disease; the above-described CD82-positive cells for use in the treatment of heart disease; and use of the above-described CD82-positive cells in production of a medicament for treating heart disease.

Other embodiments according to the present invention include a CD82-positive cell preparation method including isolating the above-described CD82-positive cells from a cell population with a fluorescence activated cell sorter (FACS) using an anti-CD82 antibody labeled with a fluorescent substance and an antibody labeled with a fluorescent substance and raised against at least one cell surface marker selected from [Cell surface marker group A] above, or with an automated magnetic cell separator (autoMACS) using an anti-CD82 antibody labeled with a labeling substance, an antibody labeled with a labeling substance and raised against at least one cell surface marker selected from [Cell surface marker group A] above, and conjugated antibodies of antibodies against the labeling substances and MACS beads (magnetic beads).

Advantageous Effects of Invention

CD73-negative, CD44-negative, CD105-negative, CD121a-negative, CD18-negative, or CD120a-negative, and CD82-positive cells (hereafter sometimes referred to as "prepared myocardial progenitor cells") according to the present invention for use as myocardial progenitor cells are specifically induced to differentiate into cardiomyocytes. Accordingly, the cells are useful for treating heart diseases including cardiomyopathies such as hypertrophic obstructive cardiomyopathy, hypertrophic non-obstructive cardiomyopathy, restrictive cardiomyopathy, arrhythmogenic right ventricular cardiomyopathy, common variable cardiomyopathy, idiopathic cardiomyopathy, dilated cardiomyopathy, ischemic cardiomyopathy simulating dilated cardiomyopathy, hypertensive cardiomyopathy, valvular cardiomyopathy, dilated phase of hypertrophic cardiomyopathy, cardiac sarcoidosis or amyloidosis relating to collagen disease or autoimmune disease, hereditary cardiomyopathy, acquired cardiomyopathy, myocarditis, postmyocarditis cardiomyopathy, drug-induced cardiomyopathy caused by drugs or intoxication, alcoholic cardiomyopathy, radiation cardiomyopathy, noncompaction of the left ventricle, muscular dystrophy-associated cardiomyopathy, mitochondrial cardiomyopathy, cardiomyopathy attributable to metabolic disorder, and postpartal cardiomyopathy; ischemic heart diseases and myocardial infarctions such as acute myocardial infarction, chronic myocardial infarction, subacute myocardial infarction, and intractable angina pectoris; cardiac failures such as chronic cardiac failure, acute cardiac failure, severe cardiac failure, and cardiac failure attributable to congenital heart disease; and arrhythmias such as congenital heart disease, ventricular arrhythmia, supraventricular arrhythmia, tachyarrhythmia, bradyarrhythmia, and lethal arrhythmia. For example, in the case of treating heart disease with cardiomyocytes, cardiomyocytes do not substantially proliferate and also exhibit a low take rate in the heart. For this reason, in general, a cardiomyocyte sheet needs to be prepared in which a sufficiently large number of cardiomyocytes for transplantation are ensured and the take rate in the heart is increased. However, prepared myocardial progenitor cells according to the present invention have a high potential of self-multiplication, a high potential of differentiation into the myocardium, and a high take rate to the myocardium, so that, in transplantation of the cells in the form of a cell sheet or cell suspension, the number of cells required can be reduced. In addition, in the case of transplantation of prepared myocardial progenitor cells according to the present invention in the form of a cell suspension, preparation of a cardiomyocyte sheet is not necessary, which is advantageous in terms of cost effectiveness or time effectiveness; furthermore, prepared myocardial progenitor cells can be administered with a catheter by injecting the cells into the affected area (heart) of a patient with heart disease, which is expected to contribute to a minimally invasive heart disease therapy that enables repeated administration.

In addition, prepared myocardial progenitor cells according to the present invention are cryopreservable because the cells having been frozen and thawed still have a high viability and a high potential of differentiation into cardiomyocytes.

BRIEF DESCRIPTION OF DRAWINGS

FIG. 8B is a phase-contrast image of the infarcted area. FIG. 8A is an image of stained cTnT and Hoechst33258 staining within the boxed region in FIG. 8B.

In FIG. 13, in the graphs in the top and middle rows and the first to third graphs from the left in the bottom row, the boxed regions "Q1", "Q2", "Q3", and "Q4" respectively represent "corresponding cell surface marker-negative CD82-positive cell group", "corresponding cell surface marker-positive CD82-positive cell group", "corresponding cell surface marker-negative CD82-negative cell group", and "corresponding cell surface marker-positive CD82-negative cell group". The ratios (%) of the number of cells of these four cell groups to the total number of cells are individually described in the corresponding regions. In FIG. 13, in the first and second graphs from the right in the bottom row, the boxed regions "Q1", "Q2", "Q3", and "Q4" respectively represent "CD82-negative corresponding cell surface marker-positive cell group", "CD82-positive corresponding cell surface marker-positive cell group", "CD82-negative corresponding cell surface marker-negative cell group", and "CD82-positive corresponding cell surface marker-negative cell group". The ratios (%) of the number of cells of these four cell groups to the total number of cells are individually described in the corresponding regions.

DESCRIPTION OF EMBODIMENTS

Figure 1:
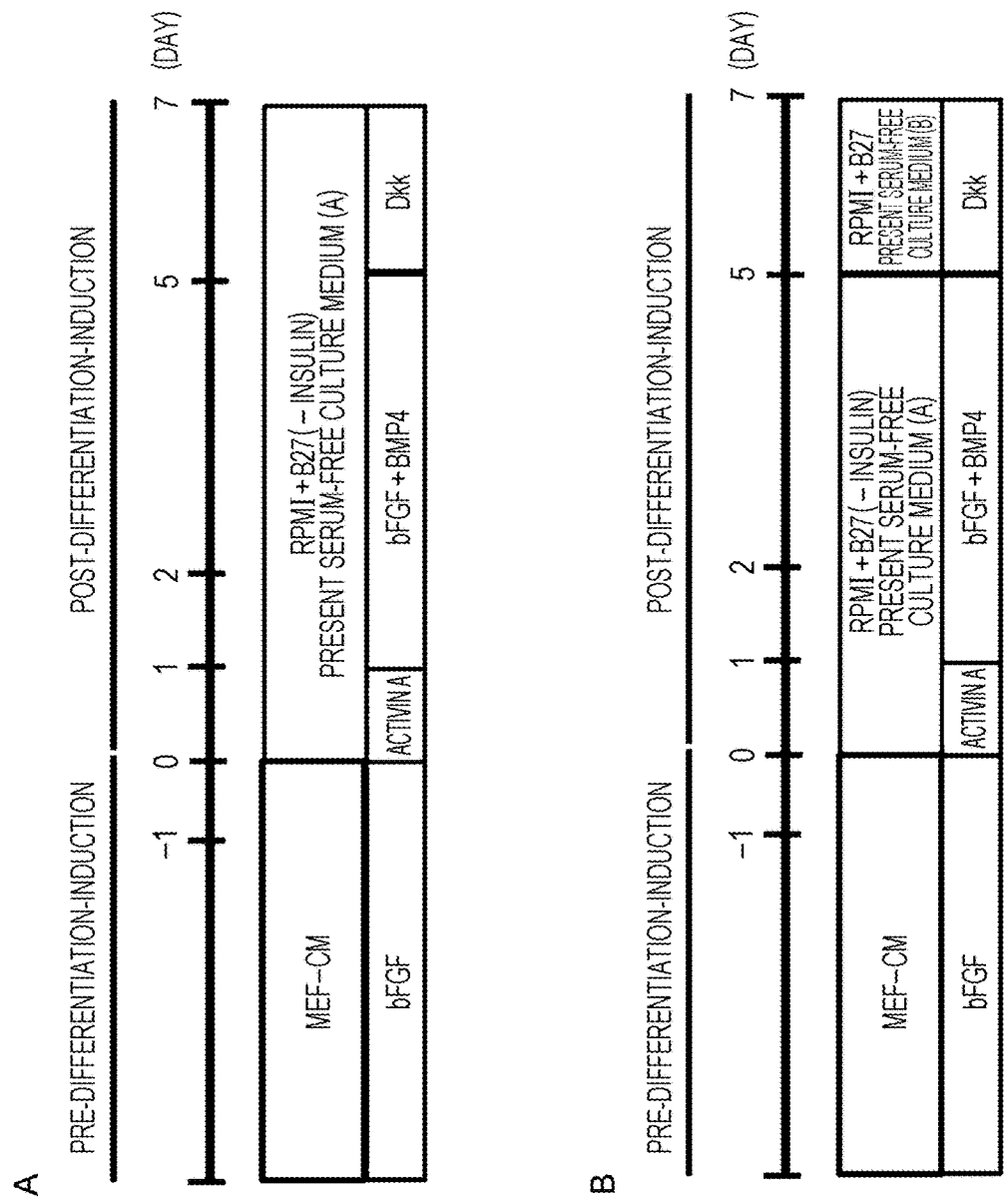
FIG. 1A schematically illustrates Modified DD protocol.
FIG. 1B schematically illustrates a protocol that is a further modification of Modified DD protocol and is used in Example (hereafter, referred to as "the present protocol").

Prepared myocardial progenitor cells according to the present invention are CD73-negative, CD44-negative, CD105-negative, CD121a-negative, CD18-negative, or CD120a-negative, and CD82-positive cells with a limitation on the application, "for use as myocardial progenitor cells". The term "CD82-positive" means that the CD (cluster of differentiation) 82 antigen is expressed on the cell surfaces. Expression of CD82 can be examined by a process of analyzing expression of mRNA of the CD82 gene, such as quantitative RT-PCR (Reverse Transcription Polymerase Chain Reaction), RT-PCR, or Southern blotting, or a process of analyzing expression of the CD82 protein, such as western blotting, flow cytometry, ELISA, EIA, or RIA.

In the present invention, the term "myocardial progenitor cell" means a cell that specifically differentiates into a cardiomyocyte under various culture conditions or in transplantation to various tissues and organs.

Specifically, the CD82-positive cells that are negative for at least one cell surface marker selected from [Cell surface marker group A] include CD82-positive cells that are negative for CD73; CD82-positive cells that are negative for CD44; CD82-positive cells that are negative for CD105; CD82-positive cells that are negative for CD121a; CD82-positive cells that are negative for CD18; CD82-positive cells that are negative for CD120a; CD82-positive cells that are negative for CD73 and CD44; CD82-positive cells that are negative for CD73 and CD105; CD82-positive cells that are negative for CD73 and CD121a; CD82-positive cells that are negative for CD73 and CD18; CD82-positive cells that are negative for CD73 and CD120a; CD82-positive cells that are negative for CD44 and CD105; CD82-positive cells that are negative for CD44 and CD121a; CD82-positive cells that are negative for CD44 and CD18; CD82-positive cells that are negative for CD44 and CD120a; CD82-positive cells that are negative for CD105 and CD121a; CD82-positive cells that are negative for CD105 and CD18; CD82-positive cells that are negative for CD105 and CD120a; CD82-positive cells that are negative for CD121a and CD18; CD82-positive cells that are negative for CD121a and CD120a; CD82-positive cells that are negative for CD18 and CD120a; CD82-positive cells that are negative for CD73, CD44, and CD105; CD82-positive cells that are negative for CD73, CD44, and CD121a; CD82-positive cells that are negative for CD73, CD44, and CD18; CD82-positive cells that are negative for CD73, CD44, and CD120a; CD82-positive cells that are negative for CD44, CD105, and CD121a; CD82-positive cells that are negative for CD44, CD105, and CD18; CD82-positive cells that are negative for CD44, CD105, and CD120a; CD82-positive cells that are negative for CD105, CD121a, and CD18; CD82-positive cells that are negative for CD105, CD121a, and CD120a; CD82-positive cells that are negative for CD121a, CD18, and CD120a; CD82-positive cells that are negative for CD73, CD44, CD105, and CD121a; CD82-positive cells that are negative for CD73, CD44, CD105, and CD18; CD82-positive cells that are negative for CD73, CD44, CD105, and CD120a; CD82-positive cells that are negative for CD44, CD105, CD121a, and CD18; CD82-positive cells that are negative for CD44, CD105, CD121a, and CD120a; CD82-positive cells that are negative for CD105, CD121a, CD18, and CD120a; CD82-positive cells that are negative for CD73, CD44, CD105, CD121a, and CD18; CD82-positive cells that are negative for CD73, CD44, CD105, CD121a, and CD120a; CD82-positive cells that are negative for CD44, CD105, CD121a, CD18, and CD120a; and CD82-positive cells that are negative for CD73, CD44, CD105, CD121a, CD18, and CD120a.

Prepared myocardial progenitor cells according to the present invention may be CD73-negative, CD44-negative, CD105-negative, CD121a-negative, CD18-negative, or CD120a-negative, and CD82-positive cells that are contained in another cell population such as CD82-negative cells. In this case, the ratio of prepared myocardial progenitor cells contained in the other cell population may be, for example, at least 4%, at least 10%, at least 30%, at least 40%, at least 50%, at least 60%, at least 70%, at least 80%, at least 85%, at least 88%, at least 90%, at least 93%, at least 95%, or at least 98%.

When a high-purity cardiomyocyte population is prepared from prepared myocardial progenitor cells according to the present invention, preferably used are isolated "CD73-negative, CD44-negative, CD105-negative, CD121a-negative, CD18-negative, or CD120a-negative, and CD82-positive cells", in other words, high-purity prepared myocardial progenitor cells. The term "high-purity cardiomyocyte population" or "high-purity prepared myocardial progenitor cells" means that the ratio of the number of cardiomyocytes or prepared myocardial progenitor cells contained in the cell population is at least 80%, preferably at least 85%, more preferably at least 88%, still more preferably at least 90%, even more preferably at least 93%, particularly preferably at least 95%, most preferably at least 98%.

Prepared myocardial progenitor cells can be isolated with a fluorescence activated cell sorter (FACS) using an anti-CD82 antibody labeled with a fluorescent substance, or with an automated magnetic cell separator (autoMACS) using an anti-CD82 antibody labeled with a labeling substance such as a fluorescent substance, biotin, or avidin, and a conjugated antibody of an antibody against the labeling substance and MACS beads (magnetic beads). Examples of the fluorescent substance include allophycocyanin (APC), phycoerythrin (PE), FITC (fluorescein isothiocyanate), Alexa Fluor 488, Alexa Fluor 647, Alexa Fluor 700, PE-Texas Red, PE-Cy5, and PE-Cy7.

The purity of prepared myocardial progenitor cells can be determined in the following manner. The anti-CD82 antibody labeled with a fluorescent substance is used to stain CD82-positive cells; a cell-nucleus-staining fluorescent substance such as Hoechst 33342 or Hoechst 33258 is used to stain living cells, or a cell-nucleus-staining fluorescent substance such as DAPI (4',6-diamidino-2-phenylindole), TO-PRO-3 Iodide Quinolinium, 4-[3-(3-methyl-2(3H)-benzothiazolylidene)-1-propenyl]-1-[3-(trimethylammonio) propyl]-, diiodide, or LIVE/DEAD Fixable Dead Cell Stain (manufactured by Life Technology Corporation) is used to stain dead cells; the number of living cells and the number of CD82-positive cells are analyzed with a FACS; and the ratio between the number of living cells and the number of CD82-positive cells is calculated to obtain the purity.

Prepared myocardial progenitor cells according to the present invention may further have a feature of being negative for at least one cell surface marker selected from [Cell surface marker group B] above and/or being positive for at least one cell surface marker selected from [Cell surface marker group C] above, a feature of being negative for at least one cell surface marker selected from [Cell surface marker group D] above and/or being positive for at least one cell surface marker selected from [Cell surface marker group E] above, or a feature of being positive for at least one cell surface marker selected from [Cell surface marker group F] above.

Expressions of cell surface markers included in [Cell surface marker group A], [Cell surface marker group B], [Cell surface marker group C], [Cell surface marker group D], [Cell surface marker group E], and [Cell surface marker group F] above can be examined through detection by a process of analyzing expression of mRNA, such as quantitative RT-PCR, RT-PCR, or Southern blotting, or a process of analyzing expression of protein, such as western blotting, flow cytometry, ELISA, EIA, or RIA.

In general, prepared myocardial progenitor cells according to the present invention are used in the state of being present in liquid or damp (wet) with liquid. Such a liquid is not particularly limited as long as it keeps CD82-positive cells viable; examples of the liquid include physiological aqueous solutions such as serum-containing or serum-free culture media, physiological saline, phosphate buffered physiological saline, tris buffered physiological saline, HEPES buffered physiological saline, Ringer's solutions (such as lactated Ringer's solution, acetated Ringer's solution, and bicarbonated Ringer's solution), and 5% aqueous glucose solution. Examples of the serum-containing culture media include culture media for culturing animal cells, containing 0.1 to 30% (v/v) serum (such as Fetal bovine serum [FBS] or Calf bovine serum [CS]) (such as DMEM, EMEM, IMDM, RPMI1640, αMEM, F-12, F-10, M-199, and AIM-V). Examples of the serum-free culture media include the above-described culture media for culturing animal cells that are supplemented with an appropriate amount (for example, 1 to 30%) of a commercially available serum replacement such as B27 supplement (-insulin) (manufactured by Life Technologies Corporation), N2 supplement (manufactured by Life Technologies Corporation), B27 supplement (manufactured by Life Technologies Corporation), or Knockout Serum Replacement (manufactured by Invitrogen Corporation).

Optionally, the serum-containing or serum-free culture media may be appropriately supplemented with one or more selected from, for example, reducing agents (such as 2-mercaptoethanol and dithiothreitol [DTT]); cell growth factors (such as insulin, Epidermal growth factor [EGF], Insulin-like growth factor [IGF], basic fibroblast growth factor [bFGF], Platelet-derived growth factor [PDGF], Vesicular endothelial growthfactor [VEGF], Hepatocyte growth factor [HGF], FGF9, bone morphogenetic protein 4 [BMP4], BMP5, activin A, stem cell factor [SCF], Dkk1 [Dickkopf-1], Wnt inhibitors [such as XAV and IWP4], Wnt activators [such as CHIR and Kenpaullone], Leukemia Inhibitory Factor [LIF], Wnt, and TGF-β); iron sources (such as transferrin); minerals (such as sodium selenite); amino acids (for example, nonessential amino acids, such as glutamine, alanine, asparagine, serine, aspartic acid, cysteine, glutamic acid, glycine, proline, and tyrosine); vitamins (such as choline chloride, pantothenic acid, folic acid, nicotinamide, pyridoxal hydrochloride, riboflavin, thiamine hydrochloride, ascorbic acid, biotin, and inositol); sugars (such as glucose); organic amines (such as putrescine); steroids (such as progesterone and β-estradiol); antibiotics (such as penicillin and streptomycin); interleukins (such as IL-1, IL-2, IL-3, and IL-6); adhesion molecules (such as heparin, heparan sulfate, collagen, and fibronectin); organic acids (such as pyruvic acid, succinic acid, and lactic acid) and salts thereof; and buffers (such as HEPES).

Prepared myocardial progenitor cells according to the present invention that have been frozen and thawed still have a high viability and a high potential of differentiation into cardiomyocytes. Thus, when prepared myocardial progenitor cells according to the present invention are preserved for a long time, the cells are preferably cryopreserved. In general, the cells are cryopreserved in a cryopreservative solution. Examples of the cryopreservative solution include the above-described physiological aqueous solutions that contain a cryoprotectant such as glycerol, dimethyl sulfoxide (DMSO), keratin hydrolysate, hydrolyzed gelatin, serum, or serum albumin. Examples of the cryopreservative solutions further include commercially available products including CELLBANKER 1, CELLBANKER 1 plus, CELLBANKER 2, and CELLBANKER 3 (all are manufactured by JUJI FIELD Inc.), TC Protector (manufactured by DS Pharma Biomedical Co., Ltd.), Bambanker hRM (manufactured by NIPPON Genetics Co, Ltd.), Freezing Medium for human ES/iPS Cells (manufactured by ReproCELL Inc.), CryoScarless DMSO-Free (manufactured by BioVerde), and StemCell Keep (manufactured by BioVerde).

Prepared myocardial progenitor cells according to the present invention can be used in the form of adherent cells on a culture vessel treated with a coating agent, in the form of suspended cells in the physiological aqueous solution or the cryopreservative solution, in the form of a cell pellet, or in the form of a mono- or multi-layer (for example, 2 to 300 layers, or 20 to 300 layers) CD82-positive cell sheet. Examples of the coating agent include Matrigel, collagen Type I, collagen Type IV, gelatin, laminin, heparan sulfate proteoglycan, entactin, fibronectin, temperature responsive polymer (PIPAAm), and combinations of the foregoing.

A heart disease therapeutic agent according to the present invention contains, as an active ingredient, preferably at a high purity, prepared myocardial progenitor cells according to the present invention, in other words, cells that specifically differentiate into cardiomyocytes under various culture conditions or in transplantation to various tissues and organs. The heart disease therapeutic agent provides the effect of treating or preventing cardiomyopathy or heart disease. Such cardiomyopathy and heart disease include various cardiomyopathies and heart diseases due to hereditary factors or loads caused by acquired factors such as inflammation or stress or due to mixed factors of the above. Examples of the cardiomyopathies include hypertrophic obstructive cardiomyopathy, hypertrophic non-obstructive cardiomyopathy, restrictive cardiomyopathy, arrhythmogenic right ventricular cardiomyopathy, common variable cardiomyopathy, idiopathic cardiomyopathy, dilated cardiomyopathy, ischemic cardiomyopathy simulating dilated cardiomyopathy, hypertensive cardiomyopathy, valvular cardiomyopathy, dilated phase of hypertrophic cardiomyopathy, cardiac sarcoidosis or amyloidosis relating to collagen disease or autoimmune disease, hereditary cardiomyopathy, acquired cardiomyopathy, myocarditis, postmyocarditis cardiomyopathy, drug-induced cardiomyopathy caused by drugs or intoxication, alcoholic cardiomyopathy, radiation cardiomyopathy, noncompaction of the left ventricle, muscular dystrophy-associated cardiomyopathy, mitochondrial cardiomyopathy, cardiomyopathy attributable to metabolic disorder, and postpartal cardiomyopathy. Examples of the heart diseases include ischemic heart diseases and myocardial infarctions such as acute myocardial infarction, chronic myocardial infarction, subacute myocardial infarction, and intractable angina pectoris; cardiac failures such as chronic cardiac failure, acute cardiac failure, severe cardiac failure, and cardiac failure attributable to congenital heart disease; and arrhythmias such as congenital heart disease, ventricular arrhythmia, supraventricular arrhythmia, tachyarrhythmia, bradyarrhythmia, and lethal arrhythmia. Prepared myocardial progenitor cells have a high potential of self-multiplication, a high potential of differentiation into the myocardium, and a high take rate to the myocardium. Accordingly, a heart disease therapeutic agent according to the present invention containing prepared myocardial progenitor cells as an active ingredient is usable for effectively treating or preventing, in particular, severe (intractable) heart disease.

The number of prepared myocardial progenitor cells according to the present invention contained in a heart disease therapeutic agent according to the present invention varies depending on the level of damage of cardiomyocytes due to heart disease or the form of prepared myocardial progenitor cells according to the present invention, and hence cannot be unconditionally determined; however, the number of the cells is normally $1\times10^4$ to $1\times10^9$, preferably $1\times10^5$ to $1\times10^8$, more preferably $1\times10^6$ to $1\times10^7$.

A method of administering a heart disease therapeutic agent according to the present invention to patients with the above-described heart diseases can be appropriately selected in accordance with the form of prepared myocardial progenitor cells contained in a heart disease therapeutic agent according to the present invention. For example, when the prepared myocardial progenitor cells contained in a heart disease therapeutic agent according to the present invention are used in the form of a cell sheet, a surgical process may be performed to attach the cell sheet to the surface of epicardium to thereby achieve transplantation into the patient's heart. Alternatively, when the prepared myocardial progenitor cells contained in a heart disease therapeutic agent according to the present invention are used in the form of adherent cells on a culture vessel treated with a coating agent, the cells may be treated with a cell dissociation solution (such as trypsin, Lysyl Endopeptidase, Pronase, pepsin, elastase, collagenase, or hyaluronidase) to dissociate the cells from the culture vessel; the cells may be resuspended in the above-described physiological aqueous solution; and the cells may be administered to the patient by, for example, insertion through a catheter, delivery into a coronary artery or vein or directly into the heart, or injection into a vein. Alternatively, when the prepared myocardial progenitor cells contained in a heart disease therapeutic agent according to the present invention are used in the form of a cell pellet, the cells may be suspended in the above-described physiological aqueous solution; and the cells may be administered to the patient by, for example, insertion through a catheter, delivery into a coronary artery or vein or directly into the heart, or injection into a vein. Alternatively, when the prepared myocardial progenitor cells contained in a heart disease therapeutic agent according to the present invention are used in the form of cryopreserved cells in the above-described cryopreservative solution, the frozen cells may be thawed in a thermostat bath at 35 to 38° C.; the cells may be subsequently resuspended in the above-described physiological aqueous solution; and the cells may be administered to the patient by, for example, insertion through a catheter, delivery into a coronary artery or vein or directly into the heart, or injection into a vein. Alternatively, when the prepared myocardial progenitor cells contained in a heart disease therapeutic agent according to the present invention are used in the form of suspended cells in the above-described physiological aqueous solution, the cells may be optionally resuspended in the above-described physiological aqueous solution; and the cells may be administered to the patient by, for example, insertion through a catheter, delivery into a coronary artery or vein or directly into the heart, or injection into a vein.

Incidentally, prepared myocardial progenitor cells according to the present invention, which are applicable to a heart disease therapeutic agent, may also be used as a source for producing a myocardial cell model.

Prepared myocardial progenitor cells according to the present invention may be prepared by the following procedures. Stem cells are first obtained. The stem cells are not particularly limited in terms of the type of organism. Examples of the type of organism include Rodentia such as mice, rats, hamsters, and guinea pigs; Lagomorpha such as rabbits; Ungulata such as pigs, cattle, goats, horses, and sheep; Carnivora such as dogs and cats; and primates such as humans, monkeys, rhesus monkeys, cynomolgus monkeys, marmosets, orangutans, and chimpanzees. Of these, preferred are mice, pigs, and humans. In particular, humans are preferred examples in the case of using, for treating heart disease, prepared myocardial progenitor cells according to the present invention.

The stem cells encompass subgroups having different differentiation potentials, such as pluripotent stem cells and multipotent stem cells. Pluripotent stem cells are cells that cannot develop into a complete organism, but have the potential of differentiating into all types of tissues or cells constituting an organism. Multipotent stem cells are cells that have the potential of differentiating into not all but several types of tissues or cells.

Examples of the pluripotent stem cells include embryonic stem cells (ES cells) isolated from early embryos; embryonic germ cells (EG cells) isolated from fetal-period primordial germ cells (for example, refer to Proc Natl Acad Sci USA. 1998, 95:13726-31); germline stem cells (GS cells) isolated from testes immediately after birth (for example, refer to Nature. 2008, 456:344-9); stem cells derived from bone marrows such as iliac bone marrow and jaw bone marrow; mesenchymal stem cells such as adipose tissue-derived stem cells; Stimulus-Triggered Acquisition of Pluripotency cells (STAP cells), which are derived from somatic cells such as lymphocytes, have pluripotency equivalent to that of ES cells, and are obtained by stimulating somatic cells to induce dedifferentiation of the somatic cells; pluripotent cells obtained by selection from mesenchymal tissue such as skin and bone marrow (Muse cells [Multi-lineage differentiating Stress Enduring cells]); and induced pluripotent stem cells (iPS), which are derived from somatic cells such as skin cells, have pluripotency equivalent to that of ES cells, and are prepared by introducing plural genes into somatic cells to induce dedifferentiation of the subject's somatic cells. Of these, preferred are iPS cells. When prepared myocardial progenitor cells according to the present invention are used for treating heart disease, in consideration of the risk of rejection due to transplantation, preferred examples are iPS cells prepared from somatic cells derived from a patient with heart disease, and iPS cells prepared from somatic cells derived from a subject (human) having the same or substantially the same Human leukocyte antigen (HLA) genotypes as a patient with heart disease. The phrase "having substantially the same HLA genotypes" means that matching in terms of HLA genotypes is to such a degree that immunoreactions against the transplanted cells can be suppressed with an immunosuppressive drug. Thus, specific examples of such somatic cells derived from a subject (human) having substantially the same HLA genotypes include somatic cells derived from a subject (human) having the same HLA genotypes in terms of three HLA genotypes of HLA-A, HLA-B, and HLA-DR, or four HLA genotypes of these three HLA genotypes and HLA-C.

ES cells can be produced by culturing inner cell mass on feeder cells such as mitomycin C-treated mouse embryo-derived primary fibroblasts [MEF], STO cells, or SNL cells in the above-described serum-containing or serum-free culture medium. The production methods of ES cells are described in, for example, WO96/22362, WO02/101057, U.S. Pat. No. 5,843,780, U.S. Pat. No. 6,200,806, and U.S. Pat. No. 6,280,718. EG cells can be produced by culturing primordial germ cells in the above-described serum-containing or serum-free culture medium containing mSCF, LIF, and bFGF (for example, refer to Cell. 1992, 70:841-847). STAP cells can be produced by treating somatic cells (such as lymphocytes) with an acidic solution (pH 4.5 to 6.0) (International Publication No. 2013/163296 pamphlet, and Obokata, H. et al., Nature 505: 676-680 (2014)). Muse cells can be produced by subjecting mesenchymal tissue such as skin and bone marrow to stress under, for example, trypsinization or hypoxic treatment to select stress-enduring cells, or by selecting cells on the basis of, as an index, expression of a surface antigen of pluripotent stem cells, SSEA-3, and further repeatedly culturing single cells being suspended to isolate the cells (Japanese Patent No. 5185443, and Proc Natl Acad Sci USA. 2010, 107: 8639-8643). iPS cells can be produced by introducing reprogramming factors such as Oct3/4, Sox2, and Klf4 (optionally further c-Myc or n-Myc) into somatic cells (such as fibroblasts or skin cells) (for example, refer to Cell. 2006, 126:663-676, Nature. 2007, 448:313-317, Nat Biotechnol. 2008, 26; 101-106, Cell. 2007, 131:861-872, Science. 2007, 318:1917-1920, Cell Stem Cells. 2007, 1:55-70, Nat Biotechnol. 2007, 25:1177-1181, Nature. 2007, 448:318-324, Cell Stem Cells. 2008, 2:10-12, Nature. 2008, 451:141-146, and Science. 2007, 318:1917-1920). Also preferred pluripotent stem cells are stem cells that are established by culturing early embryos prepared by transplanting nuclei of somatic cells (for example, refer to Nature. 1997, 385:810-813, Science. 1998, 280:1256-1258, Nature Biotechnology. 1999, 17:456-461, Nature. 1998, 394:369-374, Nature Genetics. 1999, 22:127-128, Proc. Natl. Acad. Sci. USA. 1999, 96:14984-14989), and Rideout III et al. (NatureGenetics. 2000, 24:109-110). Specific examples of the pluripotent stem cells include human ES cells such as human ES cell line H9 (WA09) and human ES cell line H1 (WA01) (National Stem Cell bank, and WISC Bank), KhES-1, KhES-2, and KhES-3 (all from Stem Cell Research Center, Institute for Frontier Medical Sciences, Kyoto University), and HES3, HES4, and HES6 (National Stem Cell bank, and Monash University); and iPS cells such as iPS cells obtained by introducing Oct3/4 gene, Klf4 gene, C-Myc gene, and Sox2 gene (Riken BioResource Center, and Kyoto University), Tic (JCRB1331), Dotcom (JCRB1327), Squeaky (JCRB1329), Toe (JCRB1338), and Lollipop (JCRB1336) (all from National Research Institute for Child Health and Development, and Department of Research on Disease Bioresources, National Institute of Biomedical Innovation, JCRB Cell Bank), UTA-1 and UTA-1-SF-2-2 (both from Tokyo University), and iPS cells obtained by introducing Oct3/4 gene, Klf4 gene, and Sox2 gene (Nat Biotechnol. 2008, 26: 101-106).

Examples of the multipotent stem cells include somatic stem cells, for example, mesenchymal stem cells that can differentiate into cells such as adipocytes, osteocytes, chondrocytes, or adipocytes; hematopoietic stem cells that can differentiate into blood cells such as leukocytes, erythrocytes, or platelets; and neural stem cells that can differentiate into cells such as neurons, astrocytes, or oligodendrocytes. Multipotent stem cells can be isolated from organisms by known methods. For example, mesenchymal stem cells can be harvested from mammalian bone marrow, adipose tissue, peripheral blood, umbilical cord blood, or the like by a known standard method. For example, hematopoietic stem cells and the like from bone marrow puncture are cultured and passaged, so that human mesenchymal stem cells can be isolated (Journal of Autoimmunity, 30 (2008) 163-171). Hematopoietic stem cells can be isolated from biological samples such as bone marrow, umbilical cord blood, spleen, liver, and peripheral blood, with a cell separator (for example, flow cytometry) and an antibody against a surface antigen of hematopoietic stem cells (for example, CD34). The multipotent stem cells can also be obtained by culturing the pluripotent stem cells under appropriate induction conditions. Incidentally, stem cells according to the present invention also encompass stem cells that are produced by new methods after filing of the present application.

Subsequently, the obtained stem cells are subjected to induction treatment of differentiation into cardiovascular cells. The method of induction treatment of differentiation into cardiovascular cells is not particularly limited as long as it enables at least induction of differentiation into myocardial progenitor cells. This method encompasses a method of performing induction treatment of differentiation into myocardial progenitor cells; and also a method of performing induction of differentiation into myocardial progenitor cells, and subsequently culturing the cells with a VEGF-containing culture medium to prepare a cell mixture of myocardial progenitor cells, endothelial cells, and wall cells (International Publication No. 2013/137491 pamphlet).

Specific examples include a method in which, according to the method described in papers (Yamashita, J. et al., Nature 408: 92-96 (2000), Yamashita, J. K. et al., FASEB J. 19: 1534-1536 (2005), and Narazaki, G., Circulation 118: 498-506 (2008)), stem cells are cultured on a collagen IV-coated dish (without LIF and without feeder cells) to cause induction of differentiation into Flk1 (vascular endothelial growth factor receptor-2, also referred to as [VEGFR2])-positive cells, which are mesoderm progenitor cells, and further the Flk1-positive cells are cultured in a culture medium containing cyclosporin-A (CSA) to cause induction of differentiation into myocardial progenitor cells (Japanese Unexamined Patent Application Publication (Translation of PCT Application) No. 2011-515064); a method in which stem cells are cultured as suspended cells in a culture medium containing EGF and bFGF to cause induction of differentiation into myocardial progenitor cells (International Publication No. 2006/093276 pamphlet); a method in which stem cells are cultured as adherent cells or suspended cells in a culture medium containing a BMP antagonist such as noggin or chordin, to cause induction of differentiation into myocardial progenitor cells (International Publication No. 2005/033298 pamphlet); a method in which stem cells are cultured in a culture medium containing Wnt-1, Wnt-3a, or Wnt-5a, GSK3β inhibitor, or a Wnt agonist that is an aminopyrimidine derivative, to activate the Wnt signaling pathway, to cause induction of differentiation into myocardial progenitor cells (International Publication No. 2007/126077 pamphlet); a method in which stem cells are cultured in a culture medium containing activin A, and subsequently cultured in a culture medium containing BMP4, to cause induction of differentiation into myocardial progenitor cells (Japanese Unexamined Patent Application Publication No. 2013-215206, and Laflamme, M. A. et al., Nat Biotechnol, 25: 1015-1024 (2007)); a method in which stem cells are cultured as adherent cells on a culture vessel treated with the coating agent (preferably, Matrigel), the coating agent (preferably, Matrigel) is further added to coat the whole stem cells with the coating agent (Matrigel sandwich method), the cells are cultured in a culture medium containing activin A, and subsequently cultured in a culture medium containing BMP4 and bFGF, to cause induction of differentiation into myocardial progenitor cells (International Publication No. 2013/137491 pamphlet); and a method in which stem cells are cultured as adherent cells on a culture vessel treated with the coating agent (preferably, Matrigel), the coating agent (preferably, Matrigel) is further added to coat the whole stem cells with the coating agent (Matrigel sandwich method), the cells are cultured in a culture medium containing activin A, subsequently cultured in a culture medium containing BMP4 and bFGF, and further cultured in a culture medium containing Dkk1, to cause induction of differentiation into myocardial progenitor cells (Uosaki H, et al, PLoS One 2011; 6: e23657, [Present Protocol] described in Example below).

Stem cells can be cultured as adherent cells on a culture vessel treated with the coating agent, or on a culture vessel coated with the feeder cells. Examples of the culture medium used for culturing stem cells include animal-cell culture media containing 0.1 to 30% (v/v) serum (such as FBS or CS) (such as DMEM, EMEM, IMDM, RPMI1640, αMEM, F-12, F-10, M-199, and AIM-V); such animal-cell culture media supplemented with an appropriate amount (for example, 1 to 30%) of a commercially available serum replacement such as B27 supplement (-insulin) (manufactured by Life Technologies Corporation), N2 supplement (manufactured by Life Technologies Corporation), B27 supplement (manufactured by Life Technologies Corporation), or Knockout Serum Replacement (manufactured by Invitrogen Corporation); and such culture media further supplemented with a differentiation inhibitory factor such as LIF, bFGF, or SCF.

Optionally, the culture media used for culturing stem cells may be appropriately supplemented with additives such as reducing agents (such as 2-mercaptoethanol and dithiothreitol [DTT]); iron sources (such as transferrin); minerals (such as sodium selenite); amino acids (for example, non-essential amino acids, such as glutamine, alanine, asparagine, serine, aspartic acid, cysteine, glutamic acid, glycine, proline, and tyrosine); vitamins (such as choline chloride, pantothenic acid, folic acid, nicotinamide, pyridoxal hydrochloride, riboflavin, thiamine hydrochloride, ascorbic acid, biotin, and inositol); sugars (such as glucose); organic amines (such as putrescine); steroids (such as progesterone and β-estradiol); antibiotics (such as penicillin and streptomycin); interleukins (such as IL-1, IL-2, IL-3, and IL-6); adhesion molecules (such as heparin, heparan sulfate, collagen, and fibronectin); organic acids (such as pyruvic acid, succinic acid, and lactic acid) or salts thereof; and buffers (such as HEPES).

The temperature at which stem cells are cultured is normally in the range of about 30° C. to about 40° C., preferably 37° C. The $CO_2$ concentration during culture is normally in the range of about 1% to about 10%, preferably about 5%. The humidity during culture is normally in the range of about 70% to about 100%, preferably in the range of about 95% to about 100%. The O2 concentration during culture may be a normal oxygen concentration (18 to 22% $O_2$), or may be a low oxygen concentration (0 to 10% $O_2$).

Subsequently, CD82-positive cells are separated from the stem cells having been subjected to the induction treatment of differentiation into myocardial progenitor cells. The term "separate" means physically taking out CD82-positive cells from the culture vessel. When CD82-positive cells are cultured as adherent cells, a treatment using the above-described cell dissociation solution is performed under a temperature condition in the range of 20° C. to 37° C. to dissociate CD82-positive cells from the culture vessel. Thus, the culture medium containing CD82-positive cells in the culture vessel can be separated into another vessel by decantation, or can be separated with a pipette or a Pipetman into another vessel. Alternatively, when CD82-positive cells are cultured as suspended cells in a culture medium, the culture medium containing CD82-positive cells in the culture vessel can be separated into another vessel by decantation, or can be separated with a Pipetman into another vessel.

The separated CD82-positive cells are examined as to whether the cells are negative for at least one cell surface marker selected from [Cell surface marker group A] above, the cells are negative for at least one cell surface marker selected from [Cell surface marker group B] above and/or positive for at least one cell surface marker selected from [Cell surface marker group C] above, the cells are negative for at least one cell surface marker selected from [Cell surface marker group D] above and/or positive for at least one cell surface marker selected from [Cell surface marker group E] above, or the cells are positive for at least one cell surface marker selected from [Cell surface marker group F] above. In the separated CD82-positive cells, expressions of the cell surface markers included in [Cell surface marker group A], [Cell surface marker group B], and [Cell surface marker group C] above can be examined through detection by a process of analyzing expression of mRNA, such as quantitative RT-PCR, RT-PCR, or Southern blotting, or a process of analyzing expression of protein, such as western blotting, flow cytometry, ELISA, EIA, or RIA.

When such separated CD82-positive cells are used to prepare high-purity cardiomyocytes, high-purity CD82- positive cells that are isolated CD82-positive cells are preferably used. As described above, CD82-positive cells can be isolated with a FACS using an anti-CD82 antibody labeled with a fluorescent substance, or with an automated magnetic cell separator (autoMACS) using an anti-CD82 antibody labeled with a labeling substance such as a fluorescent substance, biotin, or avidin, and a conjugated antibody of an antibody against the labeling substance and MACS beads (magnetic beads). Examples of the fluorescent substance include APC, PE, FITC, Alexa Fluor 488, Alexa Fluor 647, Alexa Fluor 700, PE-Texas Red, PE-Cy5, and PE-Cy7.

The timing at which induced differentiation of stem cells into CD82-positive cells occurs can be determined by detecting CD82-positive cells in cell samples at different elapsed times from induction of differentiation, by the above-described process of analyzing expression of mRNA of the CD82 gene or by the above-described process of analyzing expression of the CD82 protein.

The timing at which CD82-positive cells are separated from stem cells having been subjected to the induction treatment of differentiation varies depending on the method of induction treatment of differentiation or culture conditions, and hence cannot be unconditionally determined; however, the timing is, after the induction treatment of differentiation, normally day 1 to day 20, preferably day 2 to day 14, more preferably day 3 to day 11, still more preferably day 4 to day 11, even more preferably day 4 to day 8.

The occurrence of induced differentiation of separated CD82-positive cells (prepared myocardial progenitor cells) into cardiomyocytes can be confirmed by performing an in vitro or in vivo experiment of inducing differentiation of CD82-positive cells into cardiomyocytes, and by detecting expression of a cardiomyocyte-specific marker (such as cTnT or αMHC) by performing a process of analyzing expression of mRNA of the cardiomyocyte-specific marker gene, such as quantitative RT-PCR, RT-PCR, or Southern blotting, or a process of analyzing expression of the cardiomyocyte-specific marker protein, such as western blotting, flow cytometry, ELISA, EIA, or RIA.

Each step in the preparation method for CD82-positive cells is preferably performed as aseptic processing, for example, in a clean bench in order to avoid entry of, for example, dust and bacteria (contamination).

Hereinafter, the present invention will be described in detail with reference to Example. However, the present invention is not limited to such Example.

Example 1

Subculture of Human iPS Cells

Human iPS cells (201B6) (provided by Professor Yamanaka, Kyoto University) were passaged in a Mouse embryonic fibroblast-conditioned medium (MEF-CM) (Knockout DMEM [manufactured by Gibco] containing Knockout SR [manufactured by Gibco] and 2-ME [manufactured by Gibco]) containing 4 ng/mL bFGF (basic fibroblast growth factor) (manufactured by Wako Pure Chemical Industries, Ltd.) (hereafter, referred to as "the present MEF-conditioned medium"), so as to adhere to a culture dish (10 cm dish [manufactured by Falcon]) coated with Matrigel (1:60 dilution, manufactured by Invitrogen Corporation), at 37° C. and 5% $CO_2$.

[Present Protocol]
1) Induction of differentiation into cardiomyocytes was carried out in accordance with the present protocol (FIG. 1B), which is a further modification of Modified DD protocol (Uosaki H, et al, PLoS One 2011; 6: e23657) (FIG. 1A). Details of the present protocol will be described in 2) to 5) below.

2) Human iPS cells cultured as adherent cells were dissociated from the culture dish by incubation with a cell dissociation solution (Versene [manufactured by Invitrogen Corporation]) at 37° C. for 3 to 5 minutes. The cells were seeded into a Matrigel-coated 6-well plate (Growth Factor Reduced Matrigel, manufactured by BD Biosciences) at a density of $1 \times 10^5$ cells/cm$^2$, and cultured in the present MEF-conditioned medium for 2 to 3 days to reach about 100% confluence.

3) Matrigel (1:60 dilution, manufactured by Invitrogen Corporation) was added to the culture medium (Matrigel sandwich method). The culture medium was incubated for 24 hours, and subsequently replaced by a culture medium "RPMI+B27-insulin" (RPMI1640 [manufactured by Life Technologies Corporation] containing 2 mM L-glutamine and B27 supplement [without insulin] [manufactured by Life Technologies Corporation]; hereafter, referred to as "the present serum-free culture medium (A)") containing 100 ng/mL activin A (manufactured by R&D Systems, Inc.), to cause induction of differentiation into cardiomyocytes. Incidentally, the time when the culture medium was replaced by the present serum-free culture medium containing activin A, was defined as post-differentiation-induction day 0 (time).

4) After a 24-hour incubation, the culture medium was replaced by the present serum-free culture medium (A) containing 10 ng/mL human bFGF (hbFGF) (manufactured by Wako Pure Chemical Industries, Ltd.) and 10 ng/mL human BMP4 (hBMP4; Human bone morphogenetic protein 4) (manufactured by R&D Systems, Inc.), and an incubation was carried out to post-differentiation-induction day 5.

5) On post-differentiation-induction day 5, the culture medium was replaced by a culture medium "RPMI+B27" (RPMI1640 [manufactured by Life Technologies Corporation] containing 2 mM L-glutamine and B27 supplement [manufactured by Life Technologies Corporation]; hereafter, referred to as "the present serum-free culture medium (B)") containing 100 ng/mL Dkk1 (manufactured by R&D Systems, Inc.), and an incubation was carried out for another 48 hours (to post-differentiation-induction day 7).

[Cell Sorting and Flow Cytometry Analysis]

Cells were dissociated from the culture dish by incubation with a cell dissociation solution (AccuMax [manufactured by Innovative Cell Technologies, Inc.]) at 37° C. for 3 to 5 minutes. The cells were suspended in PBS solution containing 5% FBS and 5 mM EDTA, and then subjected to antigen-antibody reactions with antibodies labeled with labeling substances and raised against five cell surface markers (KDR, PDGFRα, CD82, CD13, and VCAM1) (refer to Table 1) for 30 minutes at 4° C. Regarding TnT expressed in the cytoplasm, the cells were fixed with a 4% PFA solution for 15 minutes, and treated with a surfactant (0.75% saponin solution [manufactured by Sigma]); an anti-cTnT antibody (primary antibody) (refer to Table 1), and a secondary antibody conjugated to a labeling fluorescent substance (refer to Table 1) were then added to the cell suspension, and antigen-antibody reactions were caused for 30 minutes at 4° C. The cells were treated with a FACS (FACS Aria II [manufactured by BD biosciences]) to achieve purification (sorting) of the cells detected with the antibodies. Expressions of cell surface markers detected by the antibodies were analyzed with a flow cytometer (FACS Aria II [manufactured by BD biosciences]).

TABLE 1

| Cell surface marker | Antibody |
| --- | --- |
| KDR | Antibody: CD309 (VEGFR-2/KDR)-PE (ES8-20E6, manufactured by Miltenyi Biotec) |
| PDGFRα | Antibody: human PDGFRα-APC (PRa292, manufactured by R&D Systems, Inc.) |
| CD82 | Antibody: human CD82-PE (ASL-24, manufactured by Biolegend, Inc.) |
| CD13 | Antibody: CD13-Biotin (22A5, manufactured by Abcam plc.) |
| cTnT | Primary antibody: cTnT (11-33, manufactured by Thermo Fisher Scientific Inc.) Secondary antibody: Zenon Alexa Fluor 488 (manufactured by Life Technologies Corporation) |
| VCAM1 | Antibody: human VCAM1-APC (STA, manufactured by Biolegend, Inc.) |

[Evaluation Method for Potential of In Vitro Differentiation into Cardiomyocytes]

The cells obtained by purification according to the method described in the above section [Cell Sorting and Flow Cytometry Analysis], were seeded into a Matrigel-coated 6-well plate (Growth Factor Reduced Matrigel, manufactured by BD Biosciences) at a density of 1 to $1.5 \times 10^5$ cells/cm$^2$, and cultured in "RPMI" (RPMI1640 [manufactured by Life Technologies Corporation] containing 2 mM L-glutamine and B27 supplement [manufactured by Life Technologies Corporation]) culture medium containing 10% FBS (hereafter, referred to as "the present serum-containing culture medium"). The cells were thus cultured in the presence of the present serum-containing culture medium, which contained the serum and allowed differentiation into cells also other than cardiomyocytes, to examine whether the cells specifically differentiate into cardiomyocytes. The cells were cultured in the presence of Y-27632 (manufactured by Wako Pure Chemical Industries, Ltd.), which is a Rho-associated protein kinase (ROCK) inhibitor, until 48 hours elapsed from the seeding in order to prevent death of seeded cells. The culture medium was replaced by the freshly prepared present serum-containing culture medium every other day. After two weeks elapsed for culturing in the present serum-containing culture medium, flow cytometry analysis was carried out in accordance with the method described in the above section [Cell Sorting and Flow Cytometry Analysis] to analyze the ratio of cardiomyocytes (cTnT-positive cells). In addition, the ratio of the cells positive for VCAM1 (CD106), which is a surface marker of cardiomyocytes identified by our group (Uosaki H, et al, PLoS One 2011; 6: e23657), was also analyzed.

[RNA Microarray Analysis]

Human iPS cells were induced to differentiate into cardiomyocytes in accordance with the method described in the above section [Present Protocol]. On post-differentiation-induction day 4 and day 5, mesoderm-derived cells (KDR-positive PDGFRα-positive cells) were purified and isolated in accordance with the method described in the above section [Cell Sorting and Flow Cytometry Analysis]. The total RNA was purified with an RNeasy Mini kit (manufactured by QIAGEN), and Superscript II Reverse Transcriptase (manufactured by Lifetechnology Corporation) was then used to synthesize cDNA. The synthesized cDNA was subjected to Cy3 fluorescent labeling with a Bioarray HighYield RNA transcript labeling kit (T7) (Enzo Life Science, Inc.). The fluorescently labeled cDNA was hybridized to a Human Genome U133 Plus2.0 Array (manufactured by Affymetrix, Inc.). This hybridization was carried out with a GeneChip Hybridization Control Kit (manufactured by Affymetrix, Inc.) and a GeneChip Fluidics Station 450 (manufactured by Affymetrix, Inc.) at 45° C. for 16 hours. Fluorescent signals were scanned with a GeneChip Scanner 3000 7G (manufactured by Affymetrix, Inc.). The obtained fluorescent signal image was subjected to image processing with GeneChip Operating Software (manufactured by Affymetrix, Inc.), and subsequently subjected to statistical analysis by RMA with GeneSpring GX (manufactured by Agilent Technologies). The cell surface marker whose expression increased or decreased during post-differentiation-induction day 4 and day 5 was identified on the basis of criteria (Fold-change >2.0, P value<0.05).

[Evaluation Method 1 for Potential of In Vivo Differentiation into Cardiomyocytes]

Human iPS cells were induced to differentiate into cardiomyocytes in accordance with the method described in the above section [Present Protocol]. On post-differentiation-induction day 6, the cells were dissociated from the culture dish by incubation with a cell dissociation solution (AccuMax [manufactured by Innovative Cell Technologies, Inc.]) at 37° C. for 3 to 5 minutes. The cells were suspended in a solution containing 1% PBS, 5 mM EDTA, and 5% FBS. An anti-CD82-PE antibody (manufactured by Biolegend, Inc.) was then added, and the suspension was incubated at room temperature for 30 minutes. Subsequently, anti-PE-MACS beads (manufactured by Miltenyi Biotec) were added, and the suspension was incubated at 4° C. for 20 minutes. The cells were rinsed twice with a solution containing 1% PBS, 5 mM EDTA, and 5% FBS, and CD82-positive cells were then isolated with an automated magnetic cell separator (autoMACS [manufactured by Miltenyi Biotec]). In addition, for the purpose of use as controls, CD13-positive cells and DGFRα-positive cells were isolated. The isolated CD82-positive cells (about $5 \times 10^6$ cells) were suspended in a mixture of 10 μL of the present serum-containing culture medium and 10 μL of Matrigel (1:60 dilution, manufactured by Invitrogen Corporation), and transplanted beneath the renal capsule of a C.B-17/lcr-scid/scidJcl mouse (from CLEA Japan, Inc.). This transplantation was carried out not to the heart but beneath the renal capsule, to thereby examine whether the cells can differentiate into cardiomyocytes even under the environment not associated with the heart. In the second post-transplantation week, the mouse was euthanized; the kidney was cut off, fixed with 4% PFA, dehydrated with 30% sucrose, then embedded in OCT Compound (manufactured by Sakura Finetek), and processed with a cryostat (manufactured by Carl Zeiss) to prepare renal capsule cryosections having a thicknesses of 6 μm. The prepared renal capsule cryosections were permeabilized with a 0.1% TritonX-100/PBS solution, and subsequently blocked with 2% skim milk. Subsequently, an antigen-antibody reaction was caused with a primary antibody (anti-cTnT-antibody [manufactured by abcam plc.] at room temperature for 1 hour or overnight, followed by an antibody reaction with a secondary antibody (Alexa Fluor 488, anti-mouse IgG antibody) at room temperature for 1 hour, followed by an antibody reaction with a conjugated antibody of an anti-human nuclear antigen [HNA] antibody [stem cells, Inc.]) and Zenon Alexa Fluor 564 (manufactured by Life Technologies Corporation) at room temperature for 2.5 hours, and staining of cell nuclei with 10 μg/mL DAPI (manufactured by Life Technologies Corporation). Confocal fluorescence images were obtained with a Zeiss LSM 710 laser scanning microscope (manufactured by Carl Zeiss).

[Evaluation Method 2 for Potential of In Vivo Differentiation into Cardiomyocytes]

Human iPS cells were induced to differentiate into cardiomyocytes in accordance with the method described in the above section [Present Protocol]. On post-differentiation-induction day 6, the cells were dissociated from the culture dish by incubation with a cell dissociation solution (AccuMax [manufactured by Innovative Cell Technologies, Inc.]) at 37° C. for 10 to 15 minutes. The cells were suspended in a solution containing 1% PBS, 5 mM EDTA, and 5% FBS. An anti-CD82-PE antibody (manufactured by Biolegend, Inc.), an anti-CD13-FITC antibody (manufactured by abcam plc.), and an anti-PDGFRα-APC antibody (manufactured by R&D Systems, Inc.) were then added, and the suspension was incubated at room temperature for 30 minutes. The cells were rinsed twice with a solution containing 1% PBS, 5 mM EDTA, and 5% FBS, and CD82-positive cells (CD82-positive CD13-positive PDGFRα-positive cells) were then isolated with a cell sorter; and, to about $3 \times 10^6$ cells, Hoechst 33258 (manufactured by Invitrogen Corporation) was added. The cells were incubated at 37° C. for 15 minutes, and the cell nuclei were stained. The resultant cells were transplanted into the heart of an F344 N-Jcl rnu/rnu rat of a myocardial infarction model produced by coronary artery legation. In the fourth post-transplantation week, the rat was euthanized; the heart was cut off and fixed with 4% PFA, dehydrated with 30% sucrose, then embedded in OCT Compound (manufactured by Sakura Finetek), and processed with a cryostat (manufactured by Carl Zeiss) to prepare heart cryosections having a thickness of 6 to 10 μm. The prepared heart cryosections were permeabilized with a 0.2% Tween20/PBS solution, and subsequently blocked with 2% skim milk. Subsequently, an antigen-antibody reaction was caused with a primary antibody (anti-cTnT-antibody [manufactured by abcam plc.] at room temperature for 1 hour or overnight, followed by staining due to an antibody reaction with a secondary antibody (Alexa Fluor 488, anti-mouse IgG antibody) at room temperature for 1 hour. Images were obtained with a BIOREVO BZ-9000 (manufactured by KEYENCE Corporation).

[Evaluation Method for Potential of Differentiation of Cryopreserved CD82-Positive Cells into Cardiomyocytes]

CD82-positive cells were isolated in accordance with the method described in the above section [Evaluation Method 1 for Potential of in Vivo Differentiation into Cardiomyocytes]. A cell cryopreservative solution (CELLBANKER 3 [manufactured by JUJI FIELD Inc.]) was added so as to satisfy $1.0 \times 10^6$ cells/mL. The solution was aliquoted into CryoELITE Cyogenic vials (manufactured by WHEATON, W985866) so as to satisfy $1.0 \times 10^6$ cells/tube. The tubes were placed into a Cryo Box (manufactured by Thermo Fisher Scientific Inc., 5025-0505), and stored in a −80° C. freezer. Subsequently, the frozen tubes were transferred into and stored in liquid nitrogen. The CD82-positive cell stock was taken out of liquid nitrogen, quickly thawed in hot water bath at 37° C., and centrifuged for removal of the supernatant (cell cryopreservative solution). The cells were rinsed with PBS, subsequently seeded into a Matrigel-coated 6-well plate (Growth Factor Reduced Matrigel, manufactured by BD Biosciences) at a density of 1 to $1.5 \times 10^5$ cells/cm², and evaluated in terms of potential of differentiation into cardiomyocytes in accordance with the method described in the above section [Evaluation Method for Potential of in Vitro Differentiation into Cardiomyocytes].

[Result 1: Determination of Timing of Occurrence of Induction to Myocardial Progenitor Cells]

The following procedure was performed in order to determine, in the course of induction of differentiation from human iPS cells into cardiomyocytes, the timing of occurrence of induction to cells having the potential of differentiation into cardiomyocytes, in other words, myocardial progenitor cells. Human iPS cells were induced to differentiate into cardiomyocytes in accordance with the method described in the above section [Present Protocol]. On post-differentiation-induction day 4 and day 5, mesoderm-derived cells (KDR-positive PDGFRα-positive cells) were purified in accordance with the method described in the above section [Cell Sorting and Flow Cytometry Analysis], and the ratio of cardiomyocytes (cTnT-positive cells) was analyzed in accordance with the method described in the above section [Evaluation Method for Potential of in Vitro Differentiation into Cardiomyocytes] (refer to FIG. 2).

Figure 2:
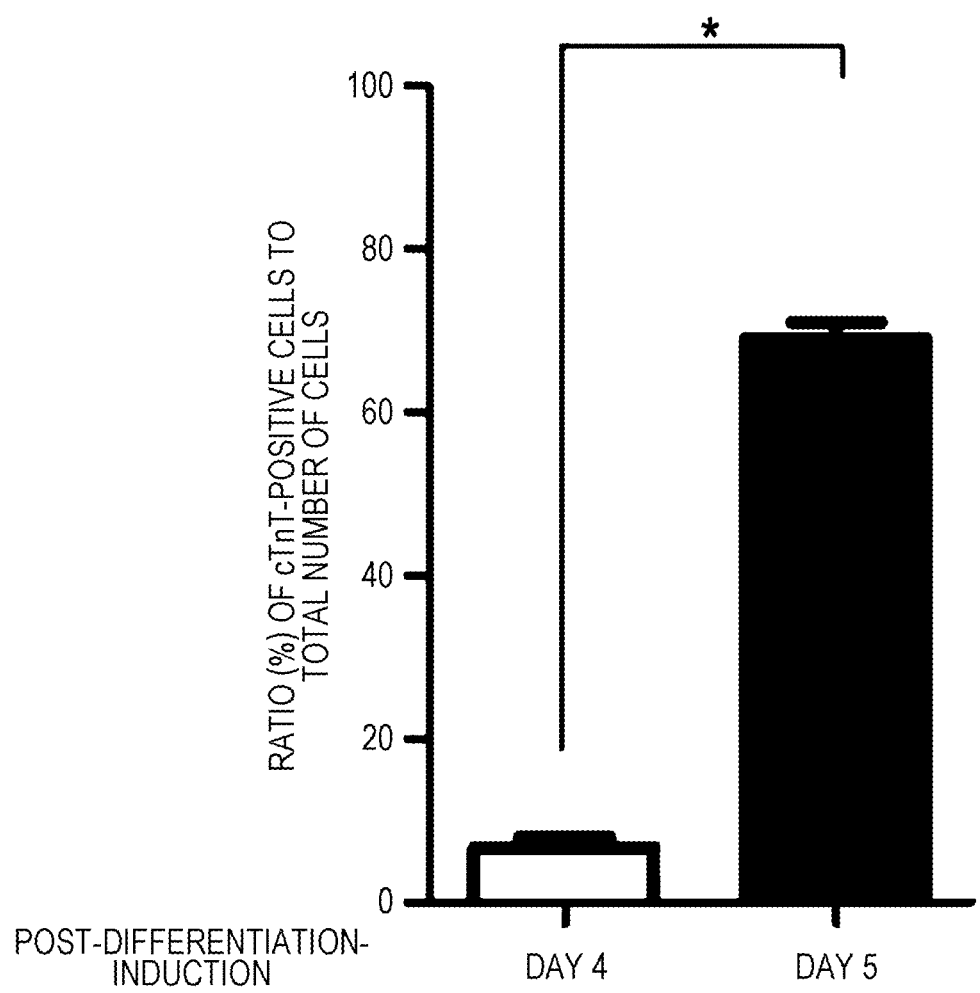
FIG. 2 is a graph illustrating analysis results of the differentiation rate into cardiomyocytes (cTnT [Cardiac toroponin T]-positive cells) when, on day 4 and day 5 after induction of differentiation of human iPS cells (Induced pluripotent stem cells) into cardiomyocytes, KDR-positive PDGFRα-positive cells are purified with a fluorescence activated cell sorter (FACS) and cultured in the presence of a serum. The ordinate axis indicates the ratio (%) of cardiomyocytes (cTnT-positive cells) to total cells (average value±standard deviation, [n=4]). The symbol "*" in FIG. 2 means the presence of a statistically significant difference (P<0.0001).

As a result, it has been revealed that KDR-positive PDGFRα-positive cells on post-differentiation-induction day 4 have a cTnT-positive cell differentiation rate of 2.6%, whereas KDR-positive PDGFRα-positive cells on post-differentiation-induction day 5 have a cTnT-positive cell differentiation rate of 69.0%, which is 27 times higher than the former differentiation rate (refer to FIG. 2). This result has demonstrated occurrence of induction to specific progenitor cells that have decided fate of differentiation into cardiomyocytes and differentiate into cardiomyocytes alone even under various conditions (hereafter, sometimes referred to as "cardiomyocyte-specific progenitor cells").

[Result 2: Identification of CD82 Whose Expression Increases During Occurrence of Induction to Myocardial Progenitor Cells]

Since Result 1 above demonstrated occurrence of induction to cardiomyocyte-specific progenitor cells during day 4 to day 5 after induction of differentiation from human iPS cells into cardiomyocytes, we considered that cells having a cell surface marker whose expression increases or decreases during this period are probably cardiomyocyte-specific progenitor cells. Thus, in order to identify a cell surface marker whose expression increases or decreases during post-differentiation-induction day 4 to day 5, analysis for a cell surface marker whose expression increases or decreases during post-differentiation-induction day 4 to day 5 was carried out in accordance with the method described in the above section [RNA microarray analysis]. As a result, CD82 has been identified. This result has suggested that CD82-expressing cells, in other words, CD82-positive cells are cardiomyocyte-specific progenitor cells.

[Result 3: Time-Dependent Changes in CD82-Positive Cells in Course of Induction of Differentiation into Cardiomyocytes]

Result 2 above demonstrated occurrence of induction to CD82-positive cells during day 4 to day 5 after induction of differentiation from human iPS cells into cardiomyocytes. CD82-positive cells after induction of differentiation were then analyzed in terms of time-dependent changes. Human iPS cells were induced to differentiate into cardiomyocytes in accordance with the method described in the above section [Present Protocol]; and, during post-differentiation-induction day 3 to day 11, expressions of CD82 and PDGFRα were analyzed with a flow cytometer in accordance with the method described in the above section [Cell Sorting and Flow Cytometry Analysis] (refer to FIG. 3).

Figure 3:
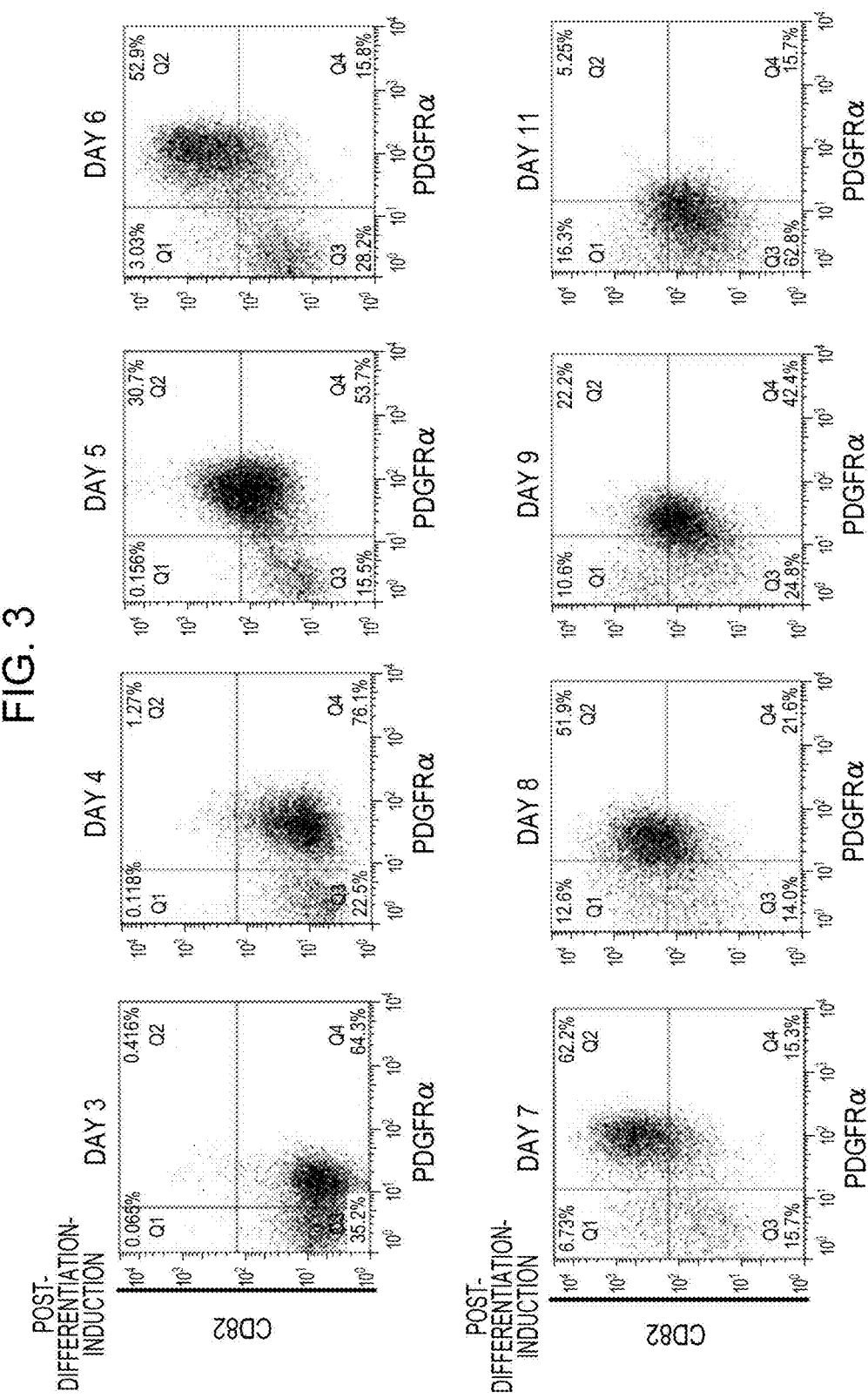
FIG. 3 includes graphs of analysis results, obtained with a flow cytometer, of expressions of CD82 (ordinate axes) and PDGFRα(abscissa axes) on day 3 to day 11 after induction of differentiation of human iPS cells into cardiomyocytes. The boxed regions "Q1", "Q2", "Q3", and "Q4" in the graphs respectively represent "CD82-positive PDGFRα-negative cell group (population)", "CD82-positive PDGFRα-positive cell group", "CD82-negative PDGFRα-negative cell group", and "CD82-negative PDGFRα-positive cell group". The ratios (%) of the number of cells of these four cell groups to the total number of cells are individually described in the corresponding regions.

As a result, the following has been demonstrated: on post-differentiation-induction day 4, induction to CD82-positive cells from the PDGFRα-positive cell group (population) begins to occur; the number of CD82-positive cells increases and, on day 6, CD82-positive cells account for about 80% of the PDGFRα-positive cell group; on day 7, the number of CD82-positive cells reaches its peak (62.2% relative to the total number of cells); and the number of CD82-positive cells rapidly decreases (to 22.2% relative to the total number of cells on day 9, and to 5.25% relative to the total number of cells on day 11) (refer to FIG. 3).

Figure 4:
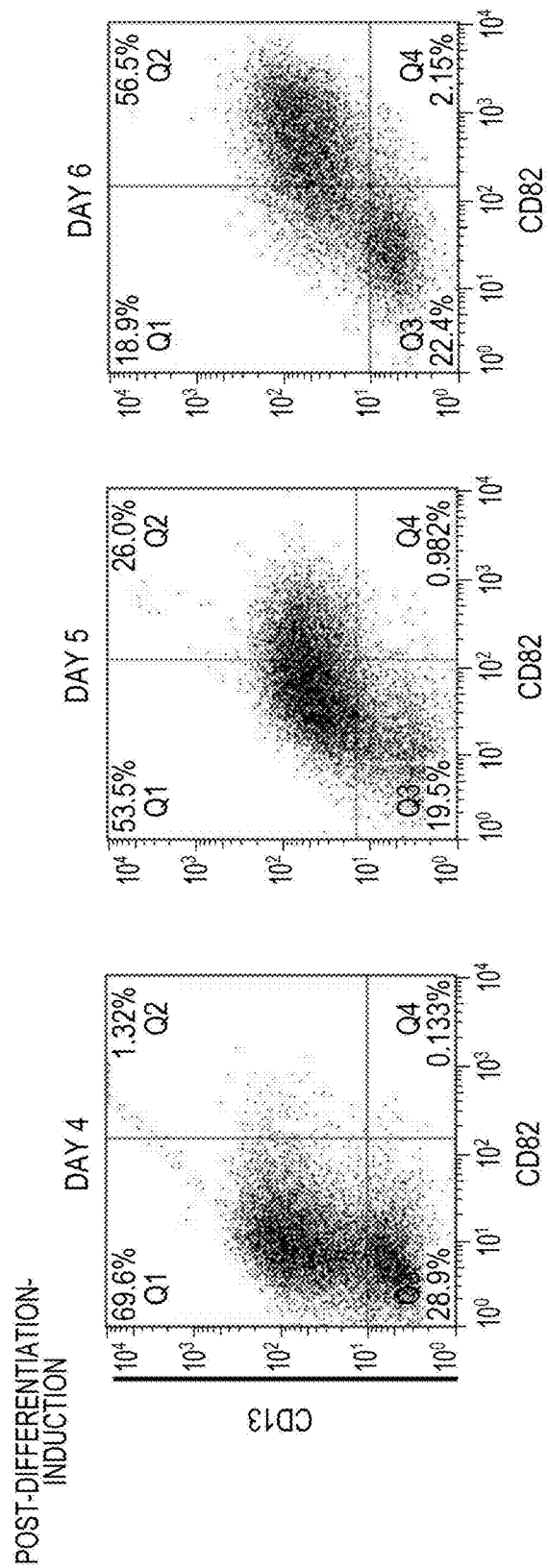
FIG. 4 includes graphs of analysis results, obtained with a flow cytometer, of expressions of CD82 (abscissa axes) and CD13 (ordinate axes) on day 4 to day 6 after induction of differentiation of human iPS cells into cardiomyocytes. The boxed regions "Q1", "Q2", "Q3", and "Q4" in the graphs respectively represent "CD82-negative CD13-positive cell group", "CD82-positive CD13-positive cell group", "CD82-negative CD13-negative cell group", and "CD82-positive CD13-negative cell group". The ratios (%) of the number of cells of these four cell groups to the total number of cells are individually described in the corresponding regions.

Similarly, expressions of CD82 and CD13 on post-differentiation-induction day 4 to day 6 were analyzed with a flow cytometer. As a result, it has been demonstrated that, on post-differentiation-induction day 4, induction to CD82-positive cells from the PDGFRα-positive cell group (population) begins to occur (refer to FIG. 4).

These results indicate that, compared with the previously reported cardiovascular progenitor cell groups that are PDGFRα-positive cells and CD13-positive cells, the degree of differentiation into cardiomyocytes is high in CD82-positive cells.

Figure 5:
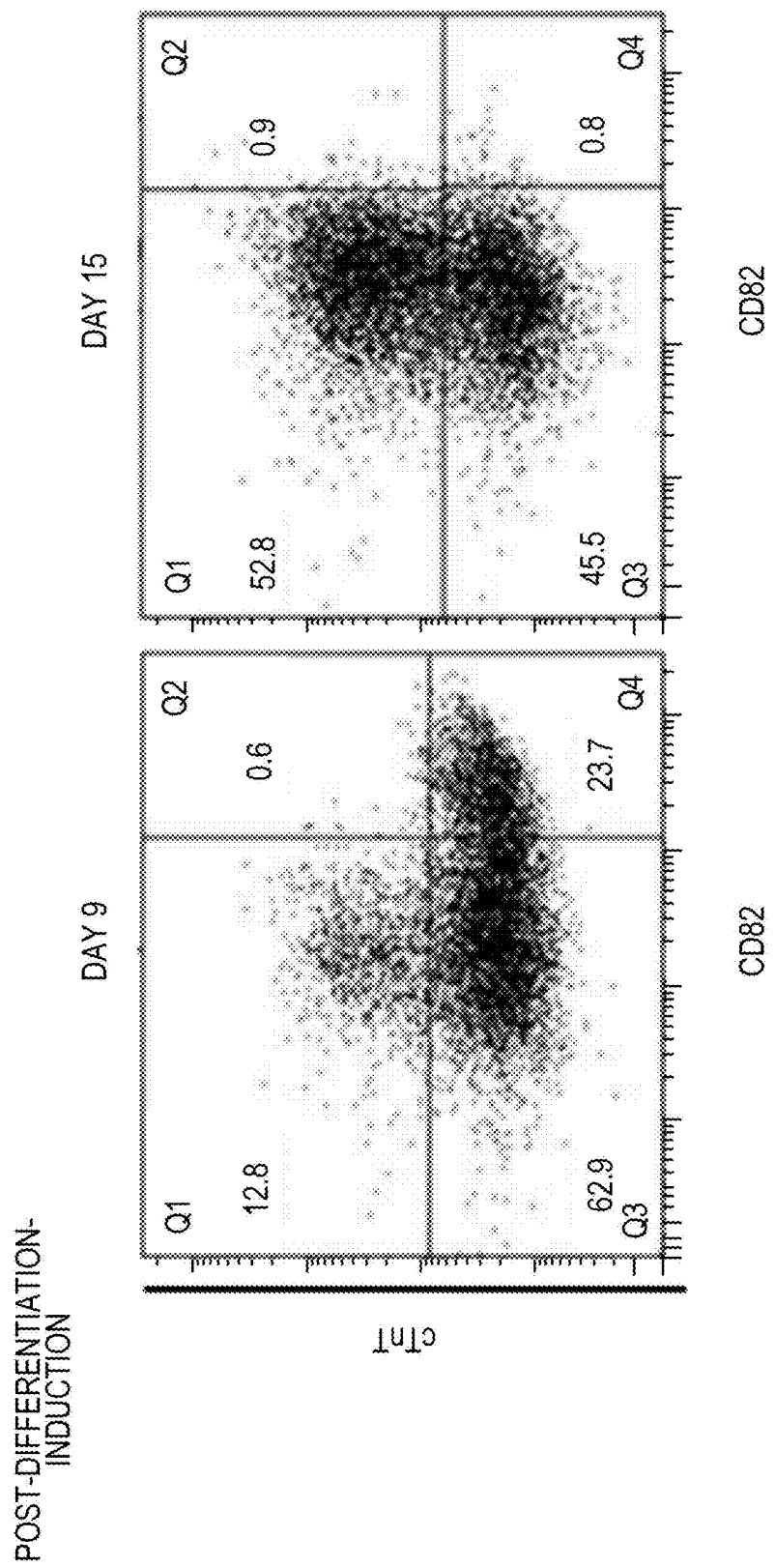
FIG. 5 includes graphs of analysis results, obtained with a flow cytometer, of expressions of CD82 (abscissa axes) and cTnT (ordinate axes) on day 9 and day 15 after induction of differentiation of human iPS cells into cardiomyocytes. The boxed regions "Q1", "Q2", "Q3", and "Q4" in the graphs respectively represent "CD82-negative cTnT-positive cell group", "CD82-positive cTnT-positive cell group", "CD82-negative cTnT-negative cell group", and "CD82-positive cTnT-negative cell group". The ratios (%) of the number of cells of these four cell groups to the total number of cells are individually described in the corresponding regions.

Similarly, expressions of CD82 and cTnT on post-differentiation-induction day 9 and day 15 were analyzed with a flow cytometer. As a result, no expression of cTnT was detected in CD82-positive cells on day 9 (refer to the left graph in FIG. 5); and no expression of CD82 was detected in cTnT-positive cells on day 15 (refer to the right graph in FIG. 5).

These results indicate that CD82 is no longer expressed after completion of differentiation into cardiomyocytes (cTnT-positive cells).

[Result 4: Evaluation for Potential of In Vitro Differentiation of CD82-Positive Cells into Cardiomyocytes]

Results 2 and 3 above suggested that CD82-positive cells are cardiomyocyte-specific progenitor cells. CD82-positive cells were then analyzed as to whether or not the cells specifically differentiate into cardiomyocytes. Human iPS cells were induced to differentiate into cardiomyocytes in accordance with the method described in the above section [Present Protocol]. On post-differentiation-induction day 5, CD82-positive CD13-positive cells and CD82-negative CD13-positive cells were individually purified in accordance with the method described in the above section [Cell Sorting and Flow Cytometry Analysis], and the ratio of cardiomyocytes (cTnT-positive cells) was analyzed in accordance with the method described in the above section [Evaluation Method for Potential of in Vitro Differentiation into Cardiomyocytes] (refer to FIG. 6).

Figure 6:
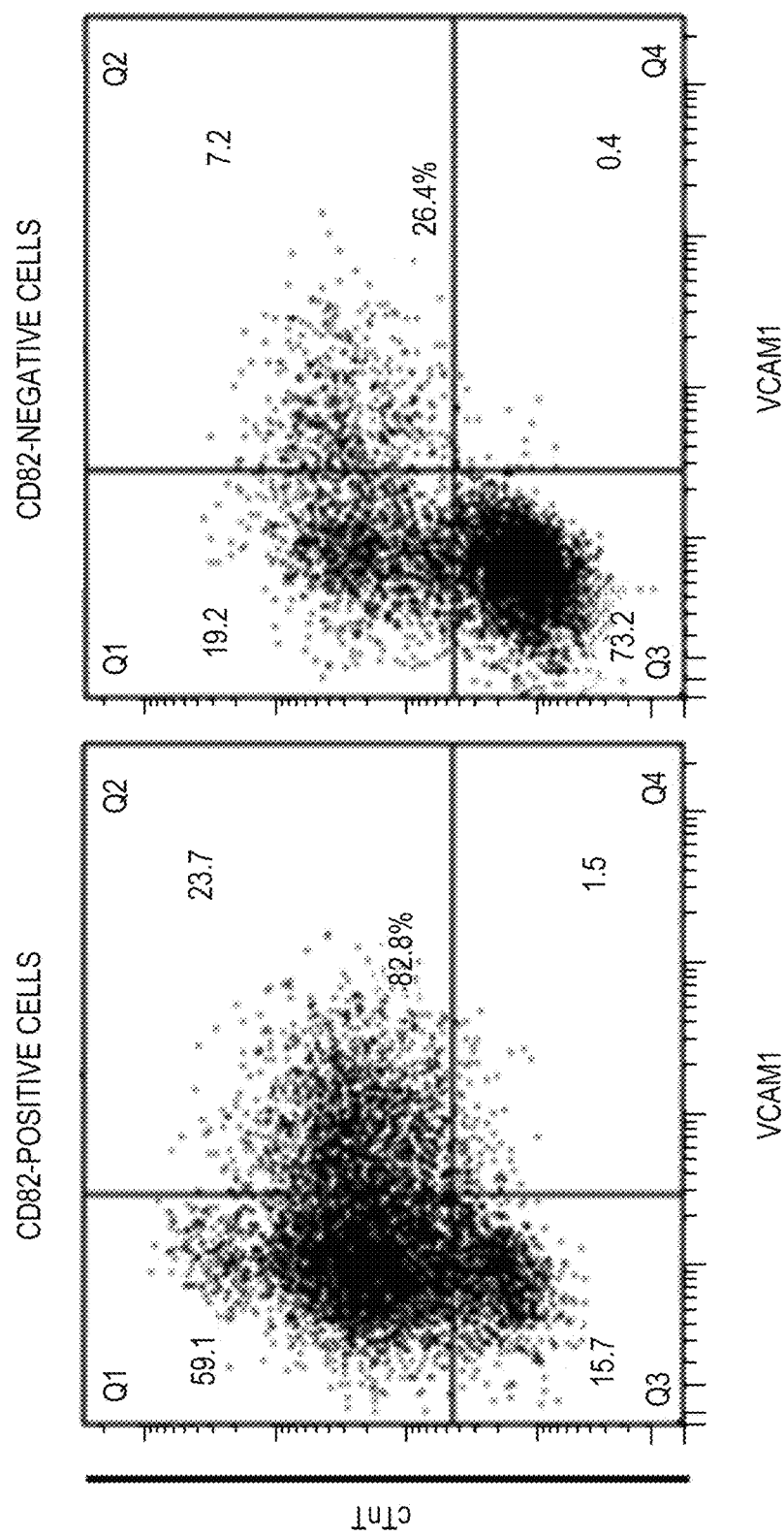
FIG. 6 includes graphs of analysis results of the differentiation rates into cardiomyocytes (cTnT-positive cells [cTnT-positive VCAM1-negative cells+cTnT-positive VCAM1-positive cells]) when, on day 5 after induction of differentiation of human iPS cells into cardiomyocytes, CD82-positive CD13-positive cells ("CD82-positive cells" in a graph) and CD82-negative CD13-positive cells ("CD82-negative cells" in a graph) were individually purified and cultured in the presence of a serum. The boxed regions "Q1", "Q2", "Q3", and "Q4" in the graphs respectively represent "cTnT-positive VCAM1-negative cell group", "cTnT-positive VCAM1-positive cell group", "cTnT-negative VCAM1-negative cell group", and "cTnT-negative VCAM1-positive cell group". The ratios (%) of the number of cells of these four cell groups to the total number of cells are individually described in the corresponding regions. In the graphs, 82.6% and 26.4% individually correspond to, in the case of culturing the CD82-positive cells and the CD82-negative cells in the presence of a serum, cTnT-positive cells (the total of the cTnT-positive VCAM1-positive cell group and the cTnT-positive VCAM1-negative cell group).

The results have revealed that the differentiation rate of CD82-negative CD13-positive cells in the presence of the serum into cTnT-positive cells is 26.4%, whereas the differentiation rate of CD82-positive CD13-positive cells into cTnT-positive cells is 82.8%, which is 3.1 times higher than the former differentiation rate (refer to FIG. 6). As a result, the in vitro experiments have demonstrated that CD82-positive cells are myocardial progenitor cells that undergo specific induction of differentiation into cardiomyocytes (cTnT-positive cells), in other words, cardiomyocyte-specific progenitor cells.

[Result 5: Evaluation for Potential of In Vivo Differentiation of CD82-Positive Cells into Cardiomyocytes]

Figure 7:
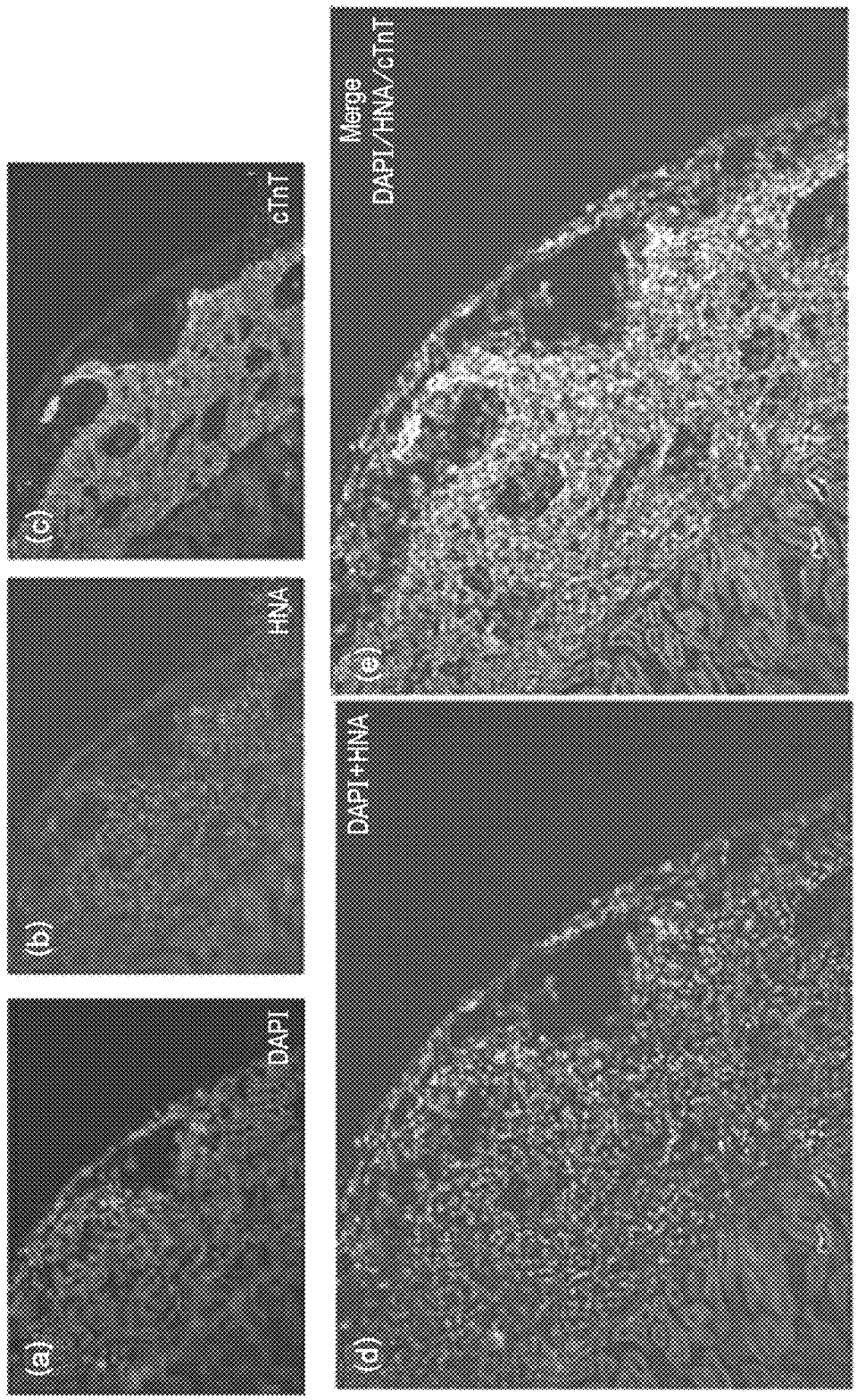
FIG. 7 includes images of results of analysis in which, on day 6 after induction of differentiation of human iPS cells into cardiomyocytes, CD82-positive cells were isolated and transplanted beneath the renal capsule of a Sevefe Combined ImmunoDeficiency (SCID) C.B-17/lcr-scid/scidJcl mouse (from CLEA Japan, Inc.); in the second post-transplantation week, tissue sections of the renal capsule were prepared, and analyzed by immunostaining: (a) an image of DAPI staining (cell nucleus), (b) an image of stained HNA (Human Nuclear Antigen) (cell derived from transplanted CD82-positive cell), (c) an image of stained cTnT (cardiomyocyte), (d) a merged image of the image of DAPI staining and the image of stained HNA, and (e) a merged image of the image of DAPI staining, the image of stained HNA, and the image of stained cTnT.

According to Result 4 above, the in vitro experiments demonstrated that CD82-positive cells are myocardial progenitor cells that undergo specific induction of differentiation into cardiomyocytes. CD82-positive cells were then examined as to whether or not the cells in vivo also undergo specific induction of differentiation into cardiomyocytes. CD82-positive cells were transplanted beneath the renal capsule of a mouse in accordance with the method described in the above section [Evaluation Method 1 for Potential of in Vivo Differentiation into Cardiomyocytes]. Among HNA-positive cells derived from the transplanted CD82-positive cells, almost all the cells (95% or more) were found to be cTnT-positive cells (cardiomyocytes) (refer to FIG. 7). On the other hand, when CD13-positive cells and PDGFRα-positive cells were transplanted beneath the renal capsules of mice, no survival of the cells beneath the renal capsules was observed.

Figure 8:
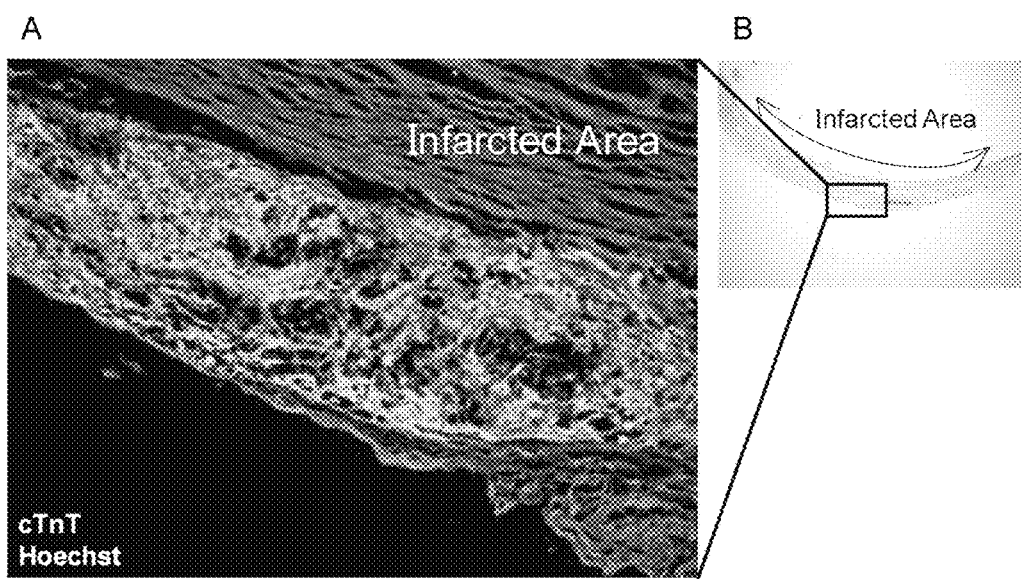
FIG. 8 includes images of results of analysis in which, on day 6 after induction of differentiation of human iPS cells into cardiomyocytes, CD82-positive cells (CD82-positive CD13-positive PDGFRα-positive cells) were isolated, and transplanted into the heart of a myocardial infarction model F344 N-Jcl rnu/rnu rat; and, in the fourth post-transplantation week, tissue sections of the heart were prepared and analyzed by immunostaining.

In addition, CD82-positive cells (CD82-positive CD13-positive PDGFRα-positive cells) were transplanted into the heart of a myocardial infarction model rat in accordance with the method described in the above section [Evaluation Method 2 for Potential of in Vivo Differentiation into Cardiomyocytes]. Among Hoechst33258-positive cells derived from the transplanted CD82-positive cells, almost all the cells (95% or more) were found to be cTnT-positive cells (cardiomyocytes) (refer to FIG. 8).

These results support the above-described in vitro results, and also indicate that CD82-positive cells enable effective engraftment to the heart, compared with previously reported cardiovascular progenitor cell groups including CD13-positive cells and PDGFRα-positive cells, and that CD82-positive cells are myocardial progenitor cells that specifically differentiate into cardiomyocytes in the heart.

[Result 6: Evaluation for Cryopreservation of CD82-Positive Cells]

Figure 9:
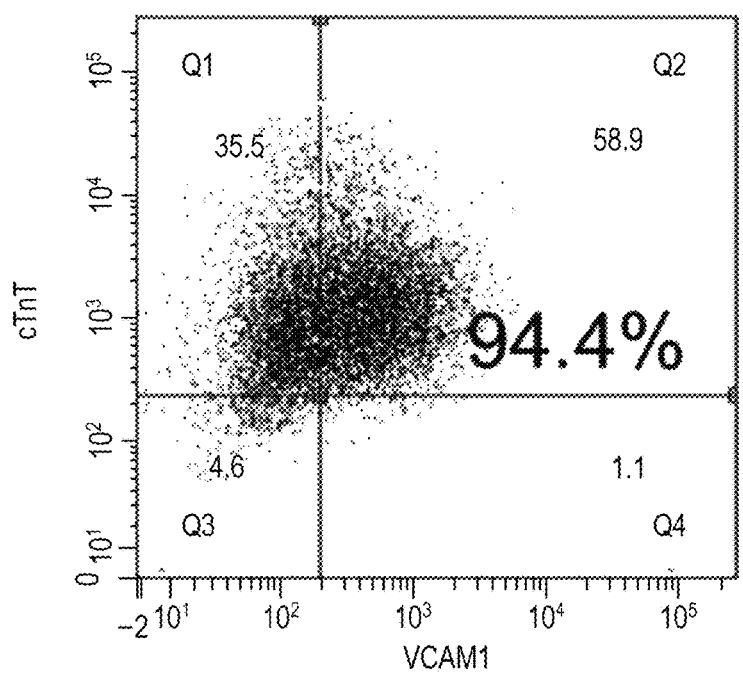
FIG. 9 is a graph of an analysis result of the differentiation rate of cryopreserved CD82-positive cells cultured in the presence of a serum, into cardiomyocytes (cTnT-positive cells [cTnT-positive VCAM1-negative cells+cTnT-positive VCAM1-positive cells]). The boxed regions "Q1", "Q2", "Q3", and "Q4" in the graph respectively represent "cTnT-positive VCAM1-negative cell group", "cTnT-positive VCAM1-positive cell group", "cTnT-negative VCAM1-negative cell group", and "cTnT-negative VCAM1-positive cell group". The ratios (%) of the number of cells of these four cell groups to the total number of cells are individually described in the corresponding regions. In the graph, 94.4% corresponds to cTnT-positive cells (total of cTnT-positive VCAM1-positive cell group and cTnT-positive VCAM1-negative cell group) in the case of culturing cryopreserved CD82-positive cells in the presence of a serum.

On the basis of Result 5 above, for therapeutically using myocardial progenitor cells that undergo specific induction of differentiation into cardiomyocytes, CD82-positive cells were examined as to whether the cells are cryopreservable or not. An evaluation for the potential of differentiation of cryopreserved CD82-positive cells into cardiomyocytes, the evaluation being carried out in accordance with the method described in the above section [Evaluation Method for Potential of Differentiation of Cryopreserved CD82-Positive Cells into Cardiomyocytes], revealed that the ratio of cTnT-positive cells (cardiomyocytes) was 94.4%, which is a high ratio (refer to FIG. 9). This result indicates that CD82-positive cells after being frozen and thawed still have a high potential of differentiation into cardiomyocytes, and the cells are cryopreservable.

[Result 7: Analysis of Expressions of Cell Surface Markers]

Human iPS cells were induced to differentiate into cardiomyocytes in accordance with the method described in the above section [Present Protocol]. On post-differentiation-induction day 4 and day 6.5, the cells were dissociated from the culture dish and caused to react with human PDGFRα-PE (PRa292, manufactured by R&D Systems, Inc.) for 30 minutes at 4° C. in accordance with the method described in the above section [Cell Sorting and Flow Cytometry Analysis]. Subsequently, in order to collectively analyze expressions of cell surface markers, antibody libraries (BD Lyoplate Screening Panels, manufactured by BD biosciences) were used to cause reactions for 30 minutes at 4° C. Expressions of cell surface markers detected were analyzed with a flow cytometer (BD LSRFortessa Cell Analyzer [manufactured by BD biosciences]).

Figure 10:
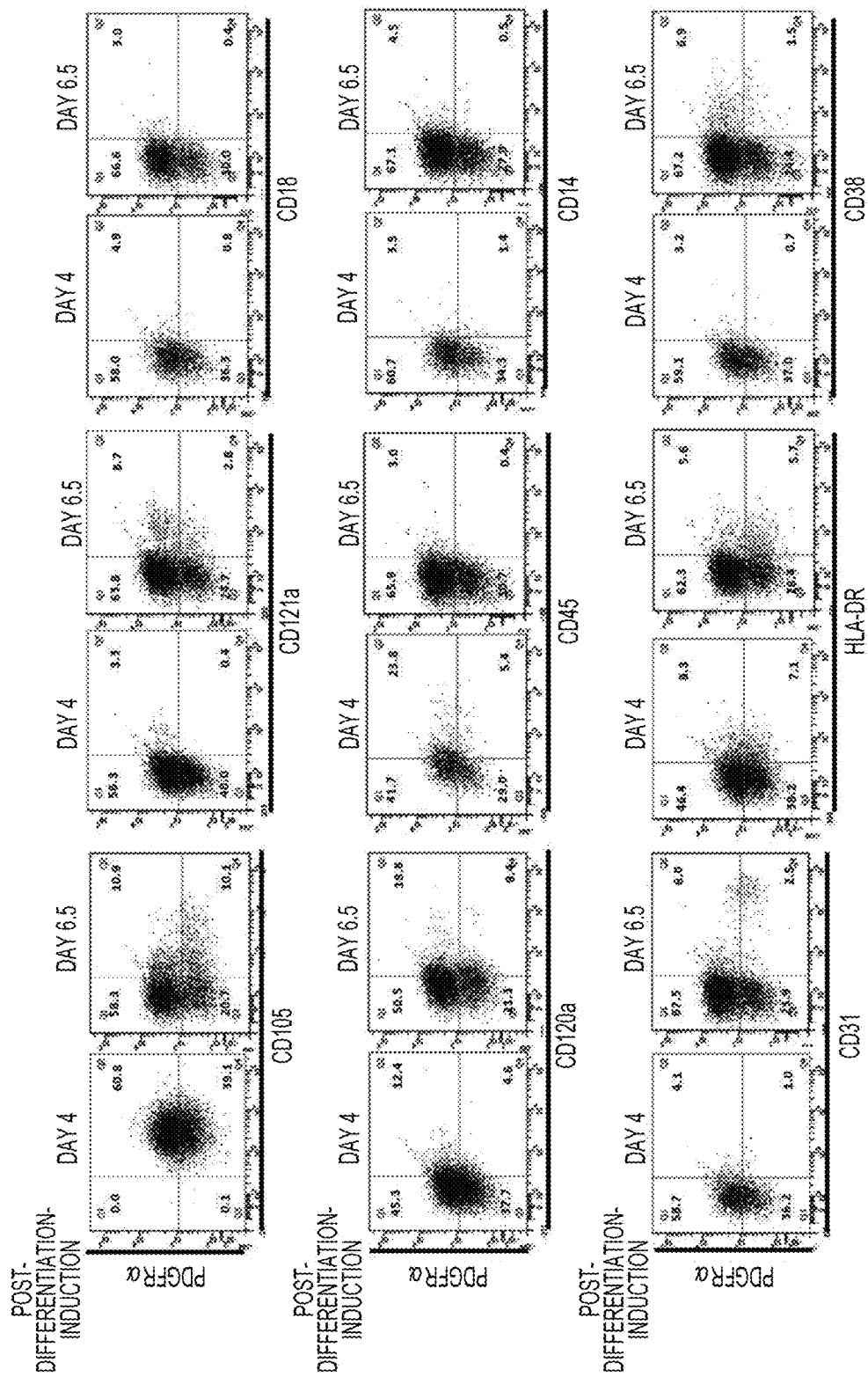
FIG. 10 includes graphs of analysis results, obtained with a flow cytometer, of expressions of PDGFRα(ordinate axes) and 9 cell surface markers (CD105, CD121a, CD18, CD120a, CD45, CD14, CD31, HLA-DR, and CD38) (abscissa axes) on day 4 and day 6.5 after induction of differentiation of human iPS cells into cardiomyocytes. The boxed regions "Q1", "Q2", "Q3", and "Q4" in the graphs respectively represent "corresponding cell surface marker-negative PDGFRα-positive cell group", "corresponding cell surface marker-positive PDGFRα-positive cell group", "corresponding cell surface marker-negative PDGFRα-negative cell group", and "corresponding cell surface marker-positive PDGFRα-negative cell group". The ratios (%) of the number of cells of these four cell groups to the total number of cells are individually described in the corresponding regions.
Figure 11:
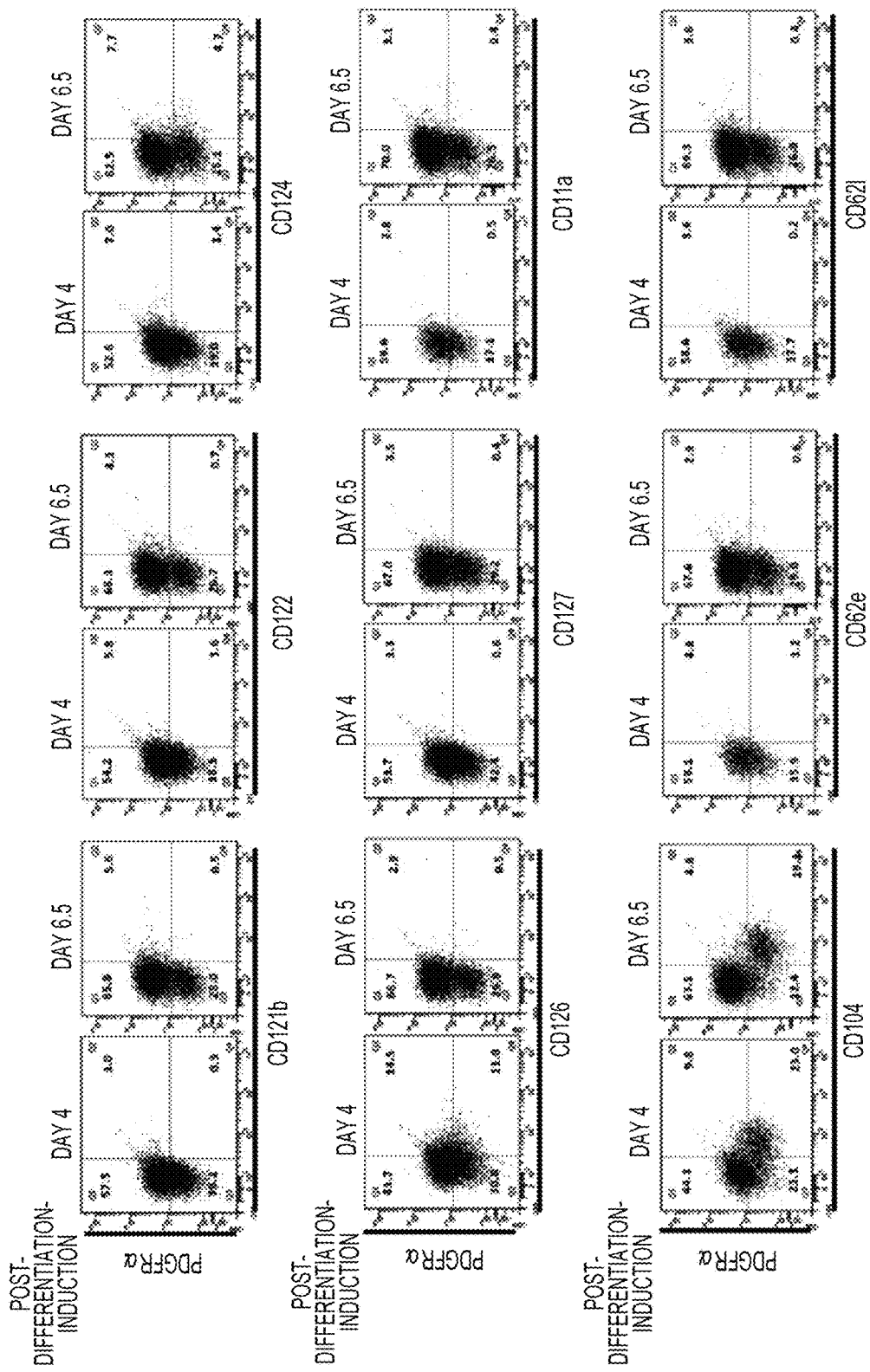
FIG. 11 includes graphs of analysis results, obtained with a flow cytometer, of expressions of PDGFRα(ordinate axes) and 9 cell surface markers (CD121b, CD122, CD124, CD126, CD127, CD11a, CD104, CD62e, and CD621) (abscissa axes) on day 4 and day 6.5 after induction of differentiation of human iPS cells into cardiomyocytes. The boxed regions "Q1", "Q2", "Q3", and "Q4" in the graphs respectively represent "corresponding cell surface marker-negative PDGFRα-positive cell group", "corresponding cell surface marker-positive PDGFRα-positive cell group", "corresponding cell surface marker-negative PDGFRα-negative cell group", and "corresponding cell surface marker-positive PDGFRα-negative cell group". The ratios (%) of the number of cells of these four cell groups to the total number of cells are individually described in the corresponding regions.
Figure 12:
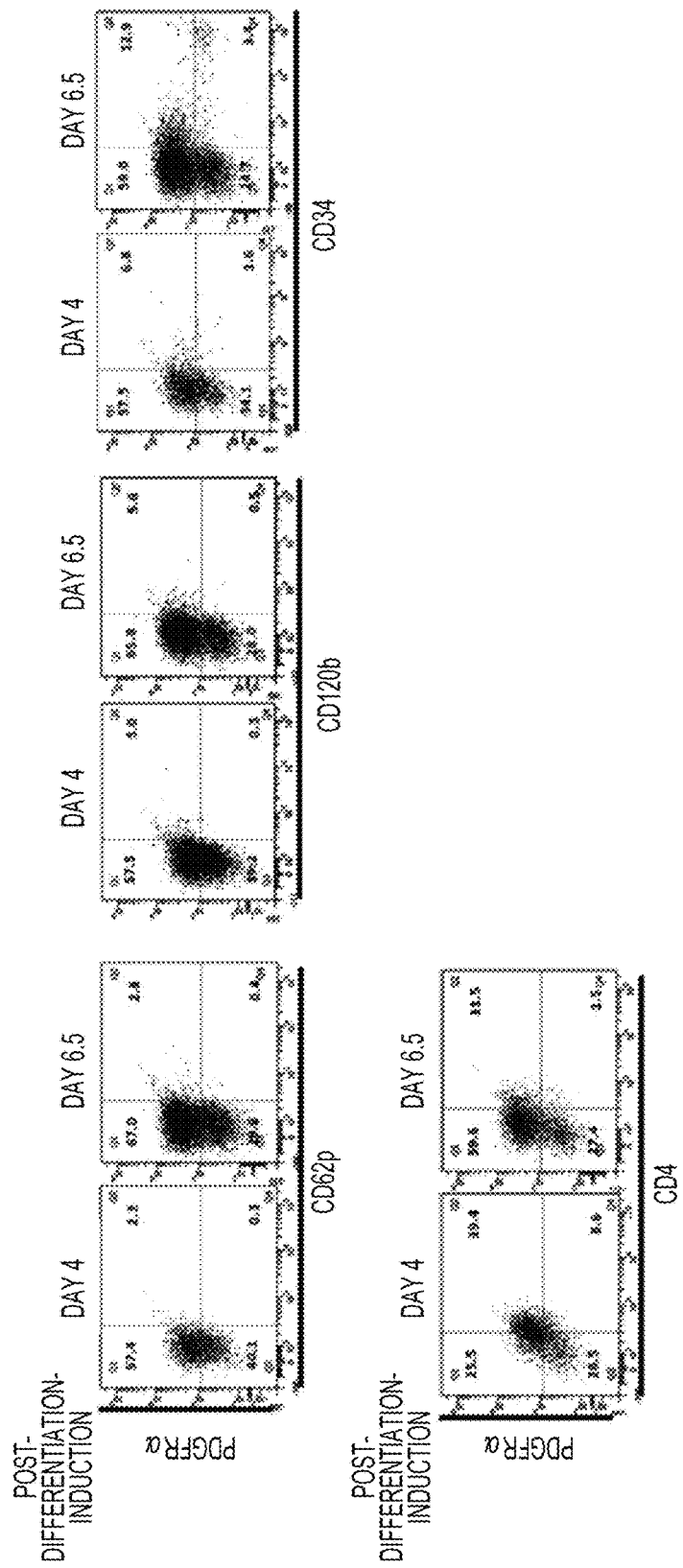
FIG. 12 includes graphs of analysis results, obtained with a flow cytometer, of expressions of PDGFRα(ordinate axes) and 4 cell surface markers (CD62p, CD120b, CD34, and CD4) (abscissa axes) on day 4 and day 6.5 after induction of differentiation of human iPS cells into cardiomyocytes. The boxed regions "Q1", "Q2", "Q3", and "Q4" in the graphs respectively represent "corresponding cell surface marker-negative PDGFRα-positive cell group", "corresponding cell surface marker-positive PDGFRα-positive cell group", "corresponding cell surface marker-negative PDGFRα-negative cell group", and "corresponding cell surface marker-positive PDGFRα-negative cell group". The ratios (%) of the number of cells of these four cell groups to the total number of cells are individually described in the corresponding regions.

The results have revealed that PDGFRα-positive cells on post-differentiation-induction day 6.5 are negative for 22 cell surface markers (CD105, CD121a, CD18, CD120a, CD45, CD14, CD31, HLA-DR, CD38, CD121b, CD122, CD124, CD126, CD127, CD11a, CD104, CD62e, CD621, CD62p, CD120b, CD34, and CD4) (refer to FIGS. 10 to 12). These results and the results in FIG. 3 indicating that about 50% of PDGFRα-positive cells on post-differentiation-induction day 6 are CD82-positive cells, as a whole indicate that CD82-positive cells are negative for these 22 cell surface markers.

In addition, human iPS cells were induced to differentiate into cardiomyocytes in accordance with the method described in the above section [Present Protocol]. On post-differentiation-induction day 6, the cells were dissociated from the culture dish and caused to react with human CD82-PE (ASL-24, manufactured by Biolegend, Inc.) or human CD82-APC (ASL-24, manufactured by Biolegend, Inc.) for 30 minutes at 4° C. in accordance with the method described in the above section [Cell Sorting and Flow Cytometry Analysis]. The cells were subsequently caused to react with antibodies against 26 cell surface markers (CD7, CD37, CD43, CD49a, CD18, CD105, CD144, STRO-1, CD177, CD73, CD44, CD117 [c-kit], CD163, CD31, CD106, ROR2, CD137L, CD140b [PDGFRb], CD166 [AL-CAM], CD180, CD252 [OX40L], CD344 [Frizzled4], CD304 [Neurophilin-1], CD118 [LIF-R], CD99R, and CD90) (refer to Table 2) for 30 minutes at 4° C. Expressions of the cell surface markers detected were analyzed with a flow cytometer (FACS (FACS Aria II [manufactured by BD biosciences])).

TABLE 2

| Cell surface marker | Antibody |
| --- | --- |
| CD7 | Antibody: CD7-FITC (CD7-6137, manufactured by Biolegend, Inc.) |
| CD37 | Antibody: CD37-FITC (M-B371, manufactured by Biolegend, Inc.) |
| CD43 | Antibody: CD43-FITC (1G10, manufactured by Biolegend, Inc.) |
| CD49a | Antibody: CD49a-FITC (TS2/7, manufactured by Biolegend, Inc.) |
| CD18 | Antibody: CD18-FITC (TS1/18, manufactured by Biolegend, Inc.) |
| CD105 | Antibody: CD105-FITC (43A3, manufactured by Biolegend, Inc.) |
| CD144 | Antibody: CD144-PE (55-7H1, manufactured by BD Parmingen) |
| STRO-1 | Antibody: STRO-1-FITC (STRO-1, manufactured by Biolegend, Inc.) |
| CD177 | Antibody: CD177-FITC (MEM-166, manufactured by Biolegend, Inc.) |
| CD73 | Antibody: CD73-FITC (AD2, manufactured by Biolegend, Inc.) |
| CD44 | Antibody: CD44-FITC (BJ18, manufactured by Biolegend, Inc.) |
| CD117 | Antibody: CD117-PE (47233, manufactured by Rand D System, Inc.) |
| CD163 | Antibody: CD163-PE (GHI/61, manufactured by BD Biosciences) |
| CD31 | Antibody: CD31-APC (WM-59, manufactured by eBioscience) |
| CD106 | Antibody: CD106-APC (STA, manufactured by Biolegend, Inc.) |
| ROR2 | Antibody: ROR2-APC (231509, manufactured by R and D System, Inc.) |
| CD137L | Antibody: CD137-PE (TKS-1, manufactured by Biolegend, Inc.) |
| CD140b | Antibody: CD140-PE (28D4, manufactured by BD Parmingen) |
| CD166 | Antibody: CD166-PE (3A6, manufactured by Biolegend, Inc.) |
| CD180 | Antibody: CD180-PE (MHR73-11, manufactured by Biolegend, Inc.) |
| CD252 | Antibody: CD252-PE (11C3.1, manufactured by Biolegend, Inc.) |
| CD344 | Antibody: CD344-PE (CH3A4A7, manufactured by Biolegend, Inc.) |
| CD304 | Antibody: CD304-PE (446921, manufactured by R and D System, Inc.) |
| CD118 | Antibody: CD118-PE (32953, manufactured by R and D System, Inc.) |
| CD99R | Antibody: CD99R-PE (MEM-1310, manufactured by abcam plc.) |
| CD90 | Antibody: CD90-APC (5E10, manufactured by Biolegend, Inc.) |

Figure 13:
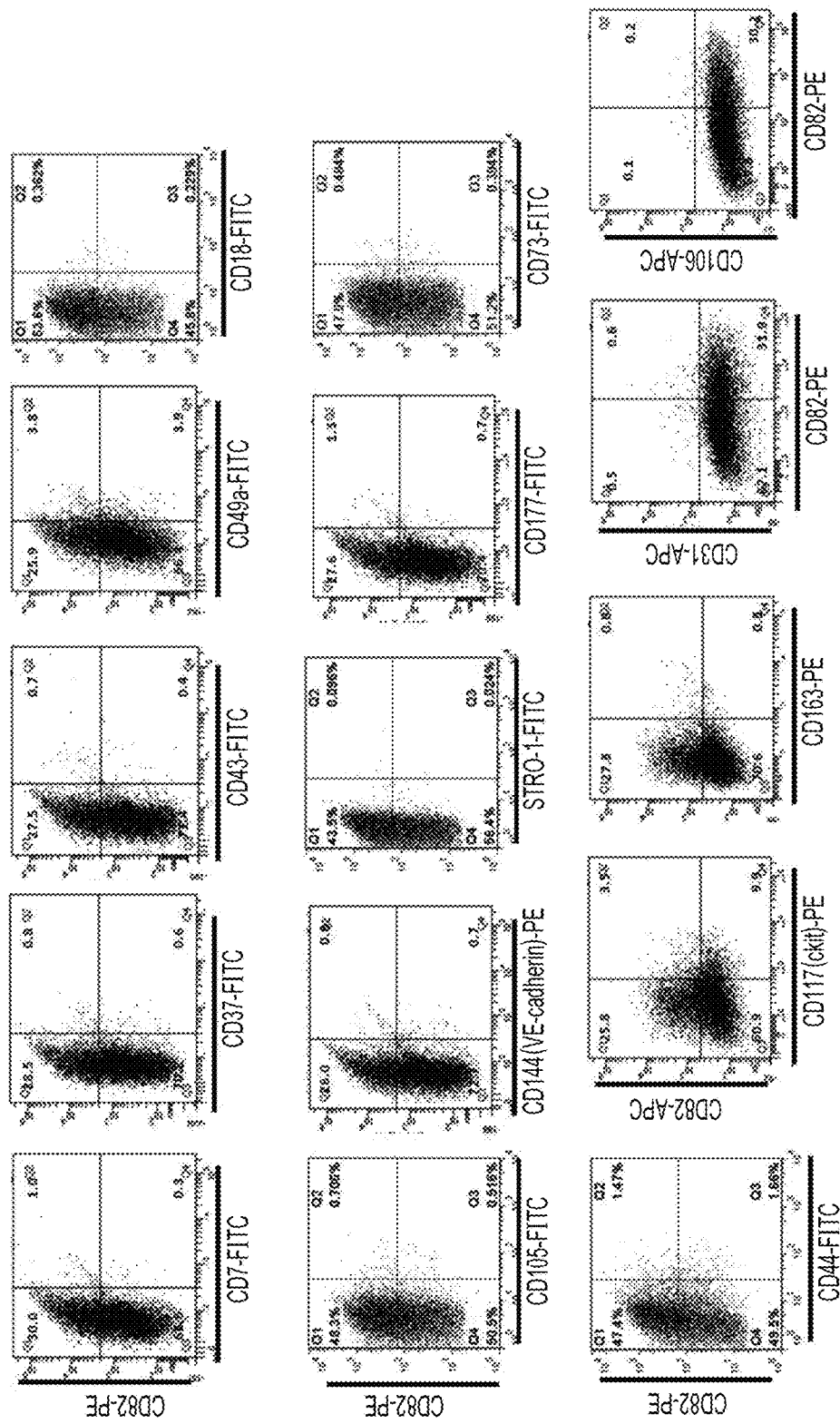
FIG. 13 includes graphs of analysis results, obtained with a flow cytometer, of expressions of CD82 and 15 cell surface markers (CD7, CD37, CD43, CD49a, CD18, CD105, CD144, STRO-1, CD177, CD73, CD44, CD117[c-kit], CD163, CD31, and CD106) on day 6 after induction of differentiation of human iPS cells into cardiomyocytes.
Figure 14:
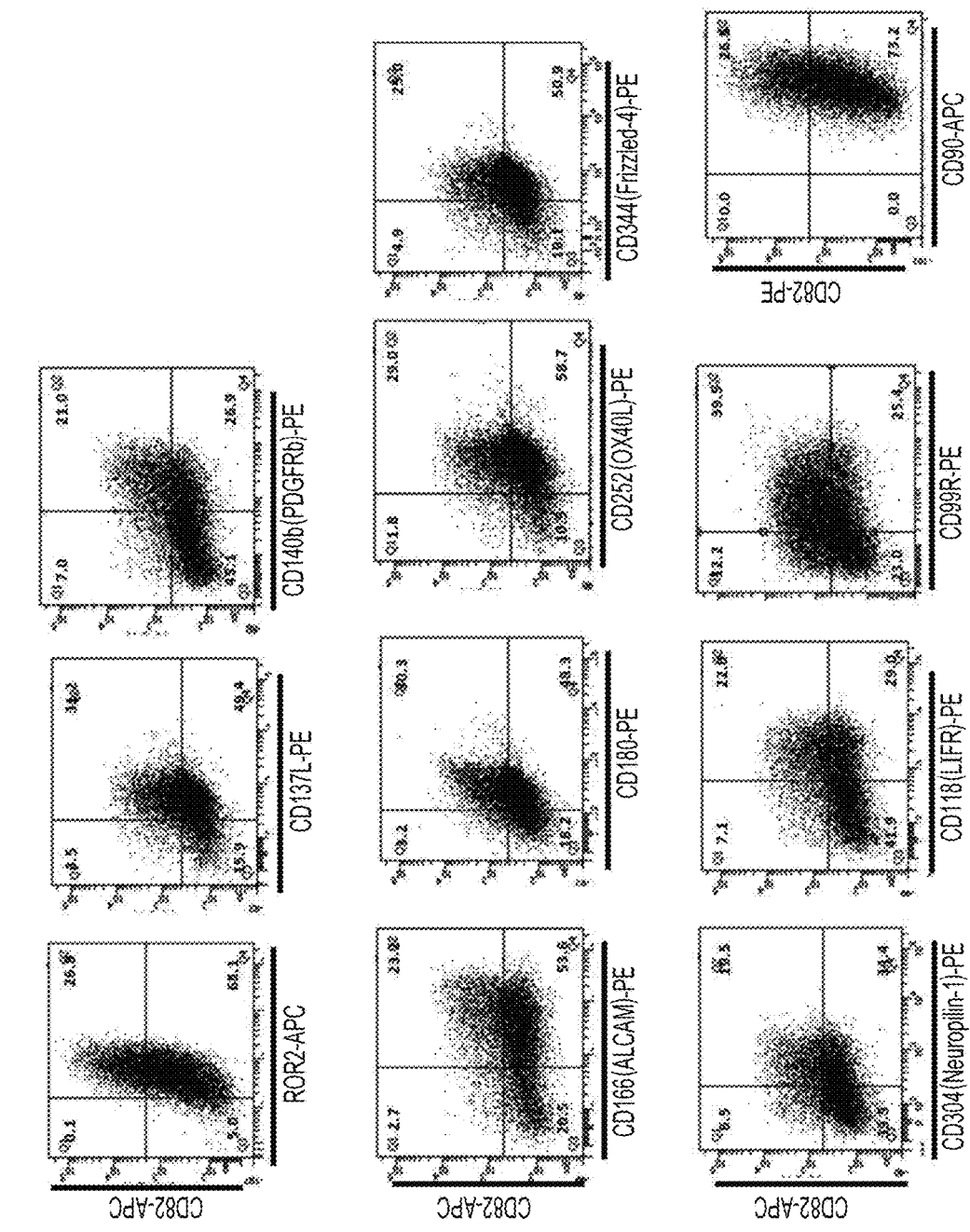
FIG. 14 includes graphs of analysis results, obtained with a flow cytometer, of expressions of CD82 (ordinate axes) and 11 cell surface markers (ROR2, CD137L, CD140b [PDGFRb], CD166 [ALCAM], CD180, CD252 [OX40L], CD344 [Frizzled4], CD304 [Neurophilin-1], CD118 [LIF-R], CD99R, and CD90) (abscissa axes) on day 6 after induction of differentiation of human iPS cells into cardiomyocytes. The boxed regions "Q1", "Q2", "Q3", and "Q4" in the graphs respectively represent "corresponding cell surface marker-negative CD82-positive cell group", "corresponding cell surface marker-positive CD82-positive cell group", "corresponding cell surface marker-negative CD82-negative cell group", and "corresponding cell surface marker-positive CD82-negative cell group". The ratios (%) of the number of cells of these four cell groups to the total number of cells are individually described in the corresponding regions.

The results have demonstrated that CD82-positive cells are negative for 15 cell surface markers (CD7, CD37, CD43, CD49a, CD18, CD105, CD144, STRO-1, CD177, CD73, CD44, CD117, CD163, CD31, and CD106) (refer to FIG. 13), and are positive for 11 cell surface markers (ROR2, CD137L, CD140b, CD166, CD180, CD252, CD344, CD304, CD118, CD99R, and CD90) (refer to FIG. 14).

INDUSTRIAL APPLICABILITY

The present invention enables preparation of myocardial progenitor cells having a potential of specific differentiation into cardiomyocytes, a high potential of self-multiplication, and a high take rate to the myocardium. Therefore, the present invention contributes to treatment of heart disease, in particular, to minimally invasive treatment of heart disease.

The invention claimed is:

1. A composition comprising:
a cell population containing a myocardial progenitor cell that is CD82-positive, and is negative for at least one cell surface marker selected from a group consisting of CD73, CD44, CD105, CD121a, CD18, and CD120a, and
a physiological aqueous solution,
wherein the myocardial progenitor cell is contained in the cell population at a ratio of at least 80%, and
wherein the physiological aqueous solution contains a cryoprotectant.

2. The composition according to claim 1, wherein the myocardial progenitor cell is a myocardial progenitor cell that is negative for at least one cell surface marker selected from a group consisting of CD7, CD37, CD43, CD144, STRO-1, CD177, and CD163; and/or is positive for at least one cell surface marker selected from a group consisting of CD137L, CD140b, CD180, CD252, CD344, CD118, and CD99R.

3. The composition according to claim 1, wherein the myocardial progenitor cell is a myocardial progenitor cell that is negative for at least one cell surface marker selected from a group consisting of CD49a, CD117, CD31, CD106, CD45, CD14, HLA-DR, CD38, CD121b, CD122, CD124, CD126, CD127, CD11a, CD104, CD62e, CD621, CD62p, CD120b, CD34, and CD4; and/or is positive for at least one cell surface marker selected from a group consisting of CD166, CD304, and CD90.

4. The composition according to claim 1, wherein the myocardial progenitor cell is a myocardial progenitor cell that is positive for at least one cell surface marker selected from a group consisting of ROR2 CD13, PDGFRα, and KDR.

5. The composition according to claim 1, being cryopreserved.

6. A heart disease therapeutic agent comprising the composition according to claim 1.

7. A method for preparing a myocardial progenitor cell, comprising steps (a) to (c) below, (a) a step of obtaining pluripotent stem cells;
(b) a step of subjecting the pluripotent stem cells to induction treatment of differentiation into cardiovascular cells; and
(c) a step of isolating, from the pluripotent stem cells having been subjected to the induction treatment of differentiation in the step (b), a myocardial progenitor cell that is CD82-positive, and is negative for at least one cell surface marker selected from a group consisting of CD73, CD44, CD105, CD121a, CD18, and CD120a, using an anti-CD82 antibody.

8. The preparation method according to claim 7, wherein the pluripotent stem cells are human pluripotent stem cells.

9. The preparation method according to claim 8, wherein the human pluripotent stem cells are human induced pluripotent stem cells.

10. The preparation method according to claim 7, wherein the induction treatment of differentiation into cardiovascular cells is induction treatment of differentiation into myocardial progenitor cells.

11. The preparation method according to claim 7, wherein the myocardial progenitor cell is a myocardial progenitor cell that is negative for at least one cell surface marker selected from a group consisting of CD7, CD37, CD43, CD144, STRO-1, CD177, and CD163; and/or is positive for at least one cell surface marker selected from a group consisting of CD137L, CD140b, CD180, CD252, CD344, CD118, and CD99R.

12. The preparation method according to claim 7, wherein the myocardial progenitor cell is a myocardial progenitor cell that is negative for at least one cell surface marker selected from a group consisting of CD49a, CD117, CD31, CD106, CD45, CD14, HLA-DR, CD38, CD121b, CD122, CD124, CD126, CD127, CD11a, CD104, CD62e, CD621, CD62p, CD120b, CD34, and CD4; and/or is positive for at least one cell surface marker selected from a group consisting of CD166, CD304, and CD90.

13. The preparation method according to claim 7, wherein the myocardial progenitor cell is a myocardial progenitor cell that is positive for at least one cell surface marker selected from a group consisting of ROR2 CD13, PDGFRα, and KDR.

14. The preparation method according to claim 7, wherein, in the step (c), the myocardial progenitor cell is isolated during day 4 to day 8 after the induction treatment of differentiation performed in the step (b).

15. The composition according to claim 2, wherein the myocardial progenitor cell is a myocardial progenitor cell that is negative for at least one cell surface marker selected from a group consisting of CD49a, CD117, CD31, CD106, CD45, CD14, HLA-DR, CD38, CD121b, CD122, CD124, CD126, CD127, CD11a, CD104, CD62e, CD621, CD62p, CD120b, CD34, and CD4; and/or is positive for at least one cell surface marker selected from a group consisting of CD166, CD304, and CD90.

16. The composition according to claim 2, wherein the myocardial progenitor cell is a myocardial progenitor cell that is positive for at least one cell surface marker selected from a group consisting of ROR2 CD13, PDGFRα, and KDR.

17. The composition according to claim 3, wherein the myocardial progenitor cell is a myocardial progenitor cell that is positive for at least one cell surface marker selected from a group consisting of ROR2, CD13, PDGFRα, and KDR.

18. The composition according to claim 15, wherein the myocardial progenitor cell is a myocardial progenitor cell that is positive for at least one cell surface marker selected from a group consisting of ROR2, CD13, PDGFRα, and KDR.

19. The preparation method according to claim 7, wherein, in the step (c), the myocardial progenitor cell is isolated so that the myocardial progenitor cell is contained in a cell population at a ratio of at least 80%.

* * * * *